(12) United States Patent
Iso-Ketola et al.

(10) Patent No.: US 10,615,794 B1
(45) Date of Patent: Apr. 7, 2020

(54) CAPACITIVE SENSOR

(71) Applicant: Forciot Oy, Tampere (FI)

(72) Inventors: Pekka Iso-Ketola, Sastamala (FI); Lari Kakkonen, Tampere (FI); Toni Liimatta, Tampere (FI); Seppo Lähdesmäki, Tampere (FI); Anne Mäkiranta, Kangasala (FI)

(73) Assignee: Forciot Oy, Tampere (FI)

( * ) Notice: Subject to any disclaimer, the term of this patent is extended or adjusted under 35 U.S.C. 154(b) by 0 days.

(21) Appl. No.: 16/396,844

(22) Filed: Apr. 29, 2019

(30) Foreign Application Priority Data

Sep. 28, 2018 (FI) .................. 20185811

(51) Int. Cl.
*H03K 17/96* (2006.01)
*G01L 1/14* (2006.01)
(Continued)

(52) U.S. Cl.
CPC ......... *H03K 17/9622* (2013.01); *A41D 1/002* (2013.01); *A61B 5/6807* (2013.01);
(Continued)

(58) Field of Classification Search
USPC .................................. 324/661–689
See application file for complete search history.

(56) References Cited

U.S. PATENT DOCUMENTS

| 5,060,527 A | 10/1991 | Burgess |
| 7,208,960 B1 | 4/2007 | Deangelis et al. |

(Continued)

FOREIGN PATENT DOCUMENTS

| EP | 2679107 A1 | 1/2014 |
| EP | 3235428 A1 | 10/2017 |

(Continued)

OTHER PUBLICATIONS

Search and examination report of the Finnish Patent Application FI20185811 issued by Finnish Patent Office dated Jan. 23, 2019 (7 pages).

(Continued)

*Primary Examiner* — Jay Patidar
(74) *Attorney, Agent, or Firm* — Berggren LLP

(57) ABSTRACT

A capacitive sensor comprising a first electrically conductive wire that is flexible and stretchable, a compressible layer, an integral reinforcement structure, and a first electrode for measuring a capacitance and coupled to the first electrically conductive wire. The first electrically conductive wire is attached to a first joint for connecting the first wire to another electrically conductive structure, such as a flexible circuit board or a connector. The capacitive sensor is dividable to a first part of the capacitive sensor and to a second part of the capacitive sensor, the first and second parts extending through the sensor in a direction (Sz) of thickness of the sensor. The first electrically conductive wire extends from the first joint via the second part of sensor to the first part of the sensor and further to the first electrode. A resilience of the second part is improved. Therefore, [A] the second part of the sensor comprises a second part of the compressible layer, wherein an in-plane stiffness of the second part of the compressible layer is less than an in-plane stiffness of the first part of the compressible layer or [B] the compressible layer does not extend to the second part of the sensor.

14 Claims, 12 Drawing Sheets

(51) Int. Cl.
*G01R 27/26* (2006.01)
*A61B 5/00* (2006.01)
*H05K 1/03* (2006.01)
*A41D 1/00* (2018.01)
*H05K 1/02* (2006.01)

(52) U.S. Cl.
CPC .......... *G01L 1/146* (2013.01); *G01R 27/2605* (2013.01); *H05K 1/0283* (2013.01); *H05K 1/0393* (2013.01)

(56) References Cited

U.S. PATENT DOCUMENTS

| | | | |
|---|---|---|---|
| 2004/0238819 | A1 | 12/2004 | Maghribi et al. |
| 2008/0174321 | A1* | 7/2008 | Kang .................. G06F 3/044 324/686 |
| 2009/0129031 | A1 | 5/2009 | Someya et al. |
| 2016/0049932 | A1* | 2/2016 | Muzzetto ............. H03K 17/955 324/686 |
| 2017/0034907 | A1 | 2/2017 | Iwase |
| 2017/0099730 | A1 | 4/2017 | Iwase |
| 2017/0181275 | A1 | 6/2017 | Dias et al. |
| 2017/0273599 | A1 | 9/2017 | Reese |
| 2017/0315165 | A1 | 11/2017 | Kawaguchi et al. |

FOREIGN PATENT DOCUMENTS

| | | |
|---|---|---|
| EP | 3282218 A1 | 2/2018 |
| FI | 127245 B | 2/2018 |
| WO | 2014204323 A1 | 12/2014 |
| WO | 2016109744 A1 | 7/2016 |
| WO | 2017033036 A1 | 3/2017 |
| WO | 2017044617 A1 | 3/2017 |
| WO | 2018011464 A1 | 1/2018 |
| WO | 2018093275 A1 | 5/2018 |
| WO | 2019022619 A1 | 1/2019 |

OTHER PUBLICATIONS

Search report of the European Patent Application 19397512.5 issued by European Patent Office dated Oct. 10, 2019 (13 pages).
Search report of the corresponding International Patent Application No. PCT/FI2019/050689 issued by European Patent Office dated Nov. 13, 2019 (5 pages).

* cited by examiner

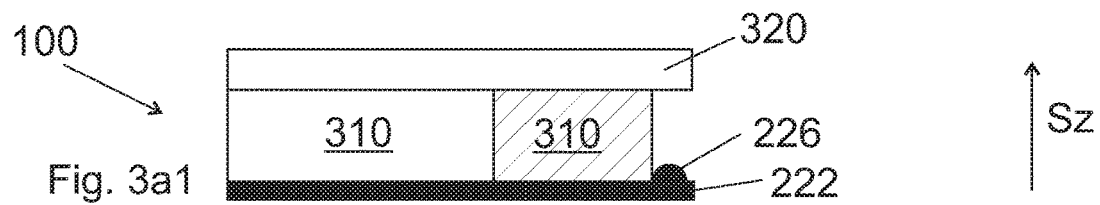
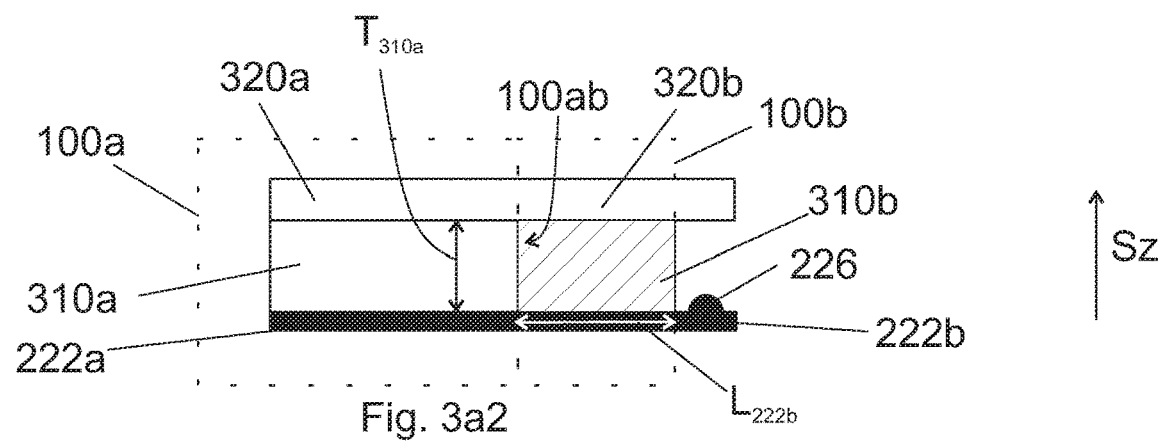
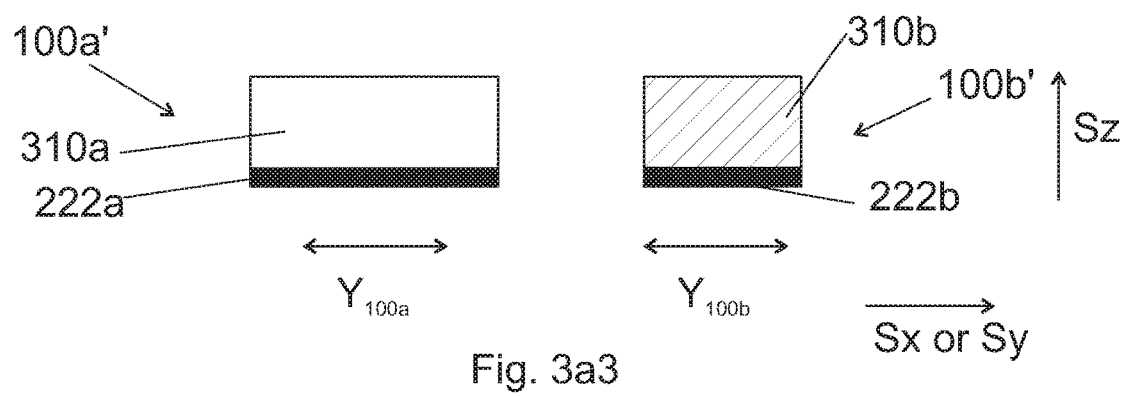
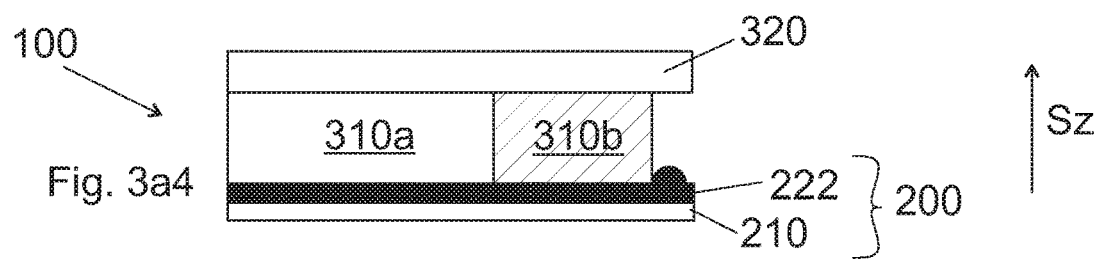

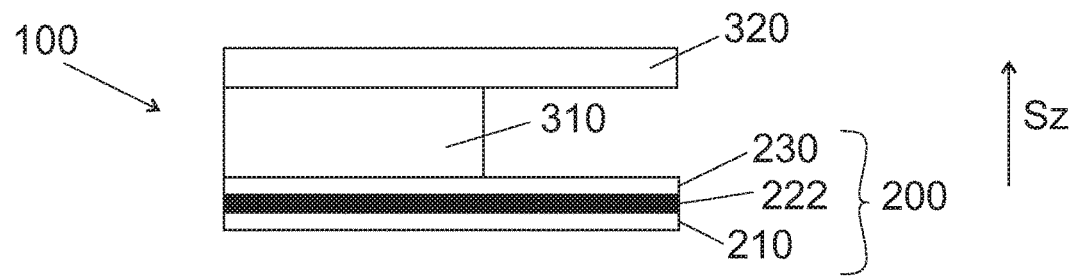
Fig. 3b1
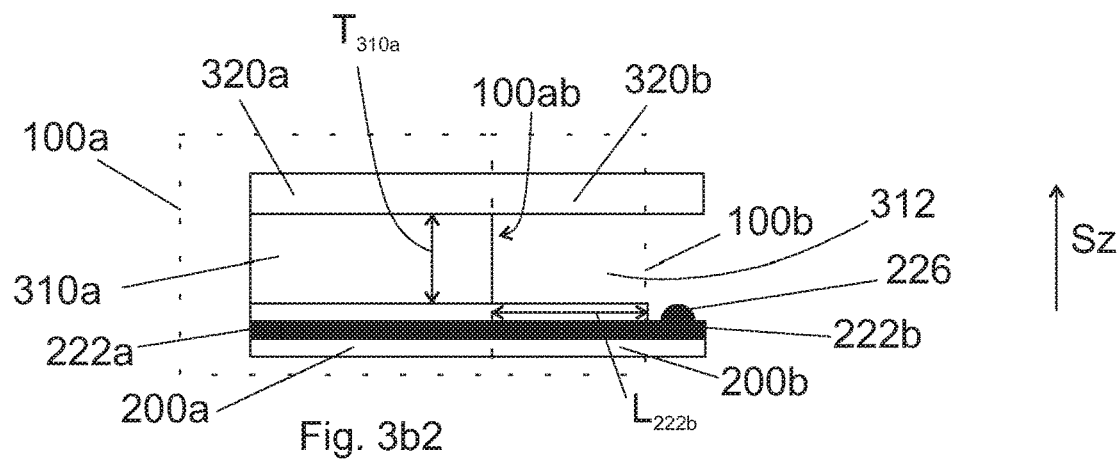
Fig. 3b2
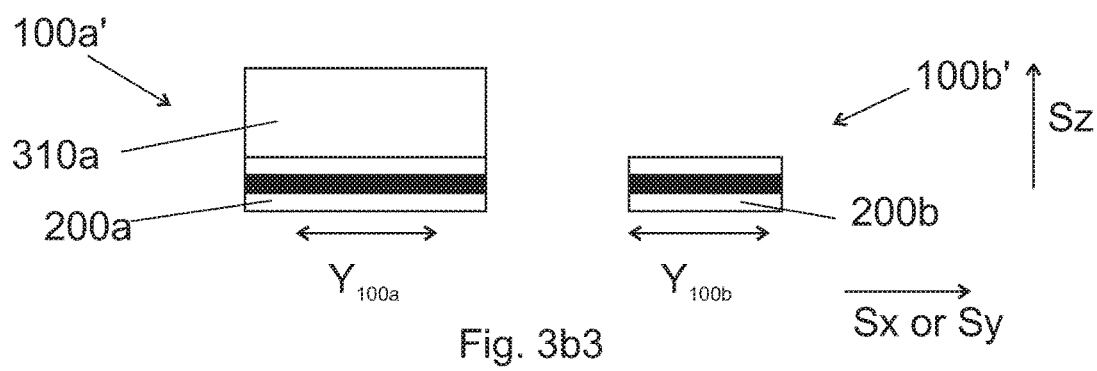
Fig. 3b3
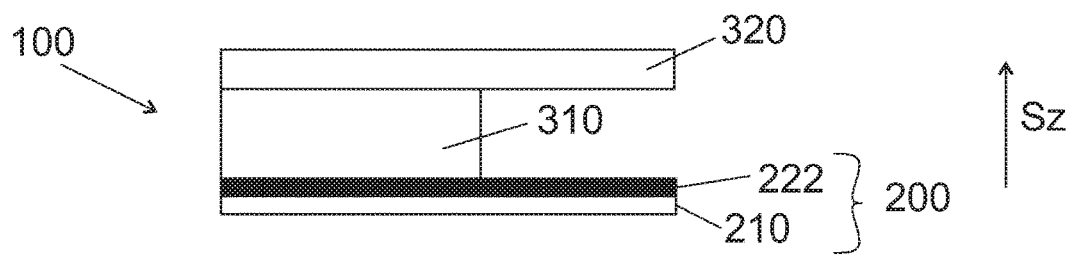
Fig. 3b4

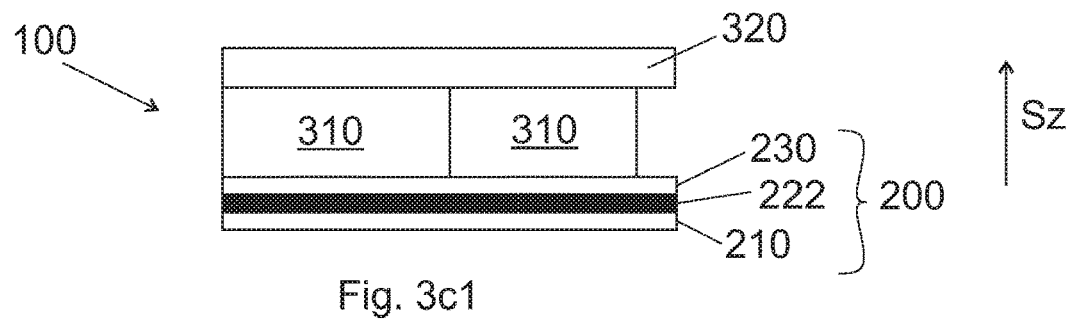
Fig. 3c1
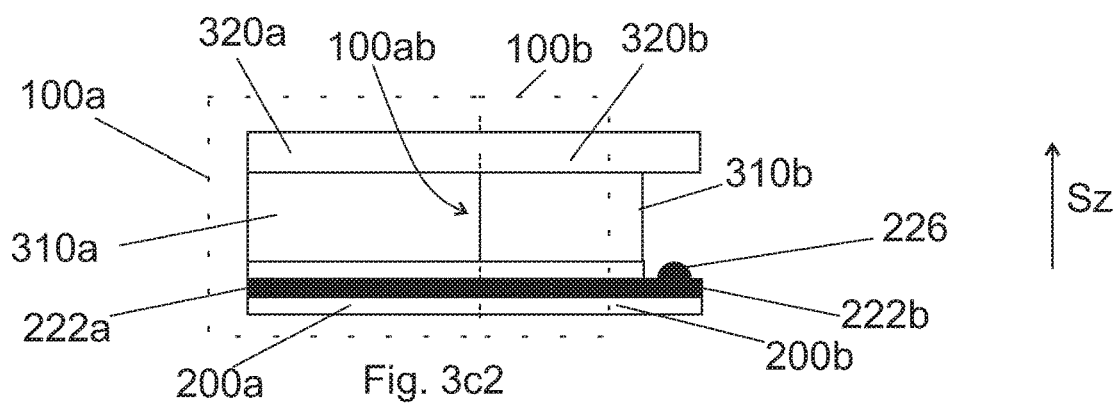
Fig. 3c2
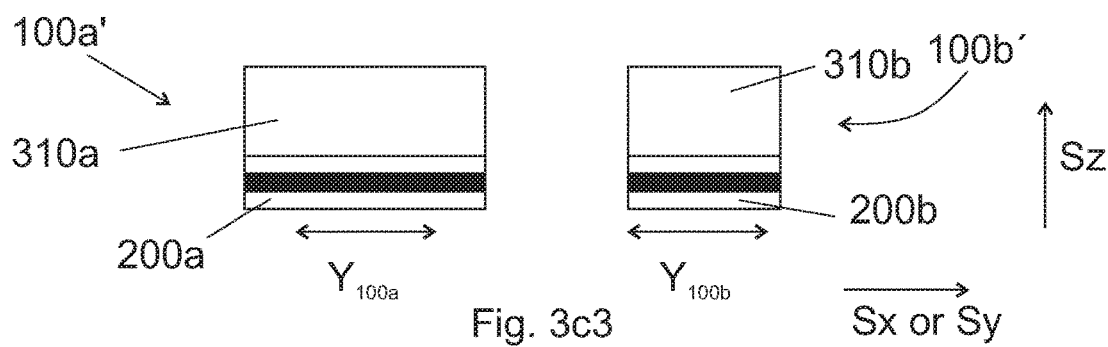
Fig. 3c3
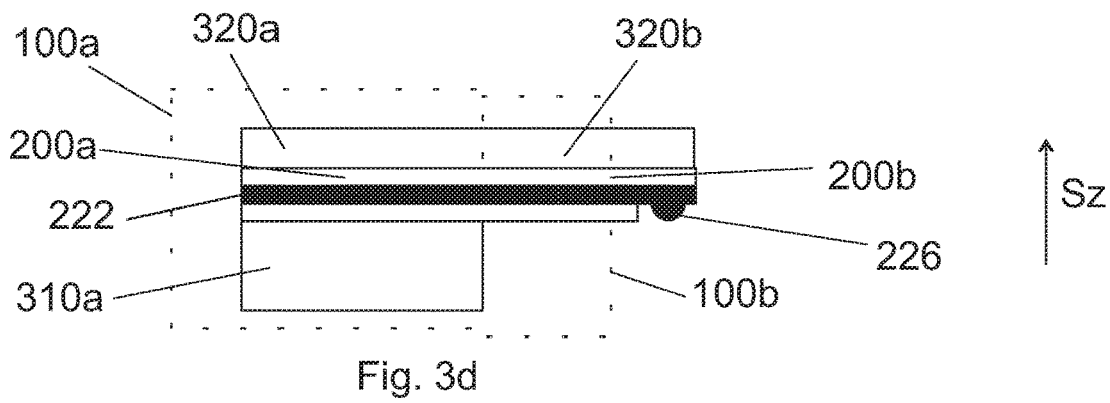
Fig. 3d

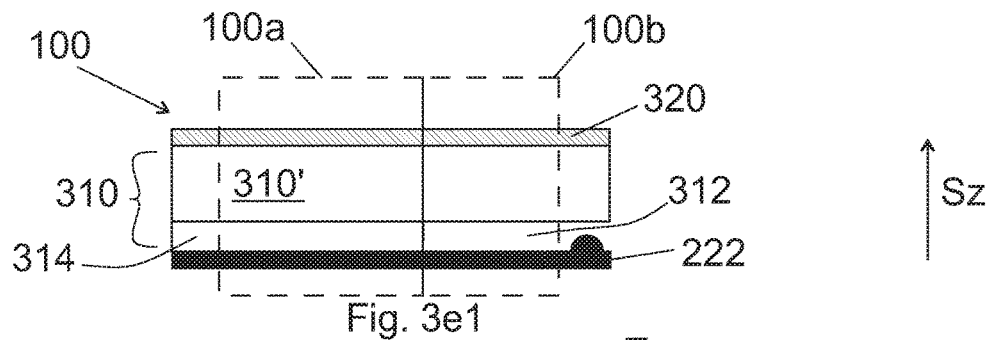
Fig. 3e1
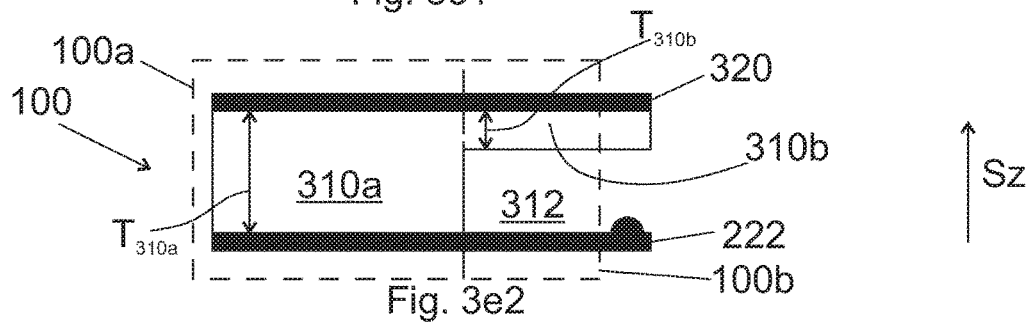
Fig. 3e2
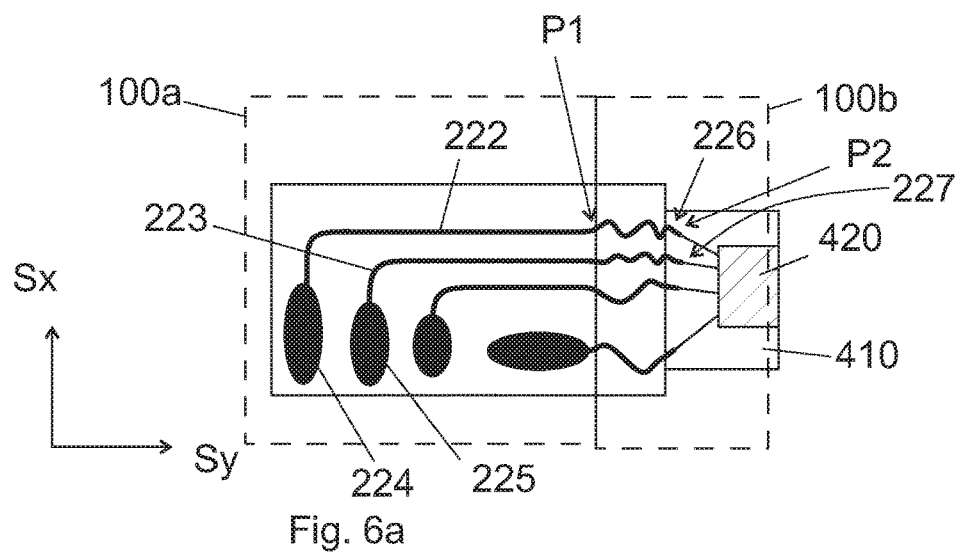
Fig. 6a
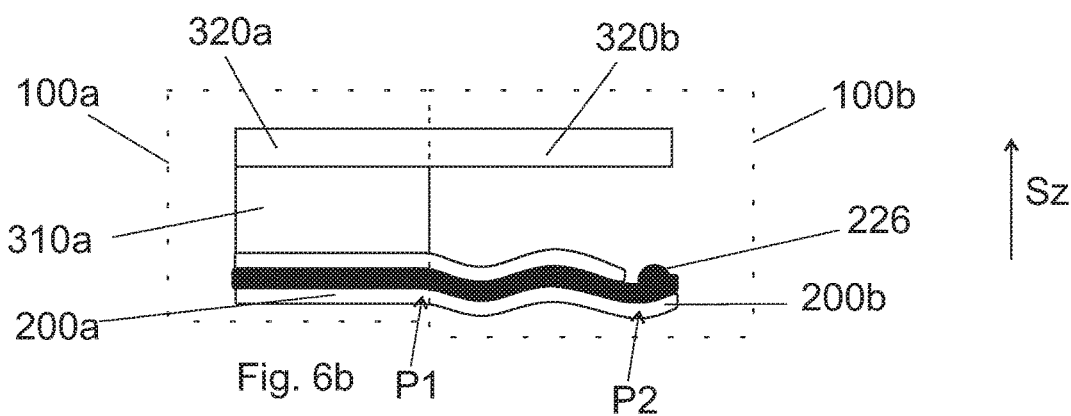
Fig. 6b

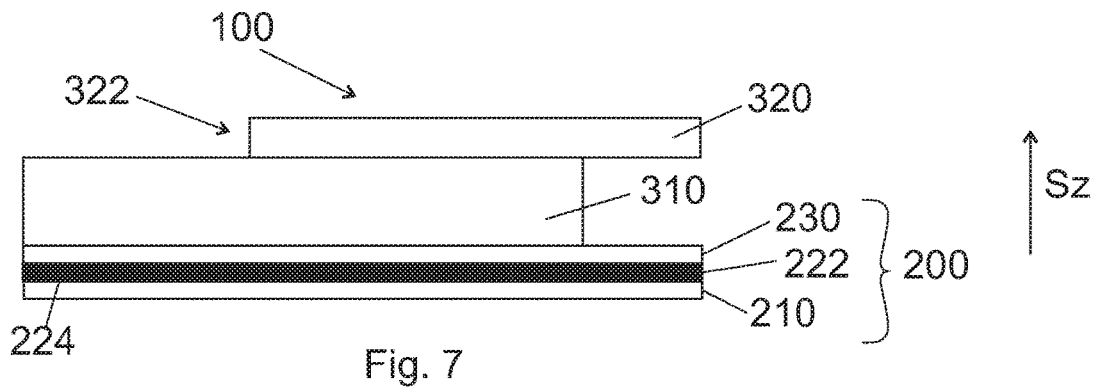
Fig. 7
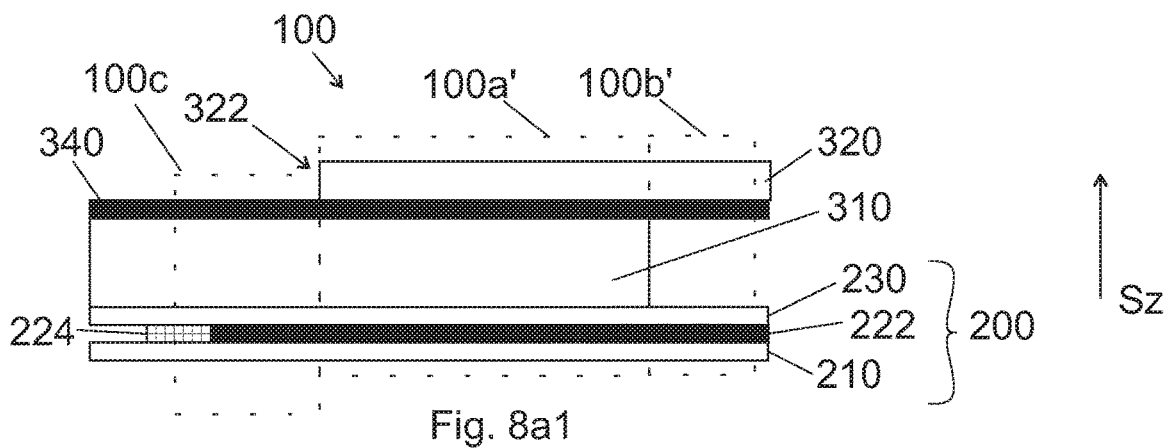
Fig. 8a1
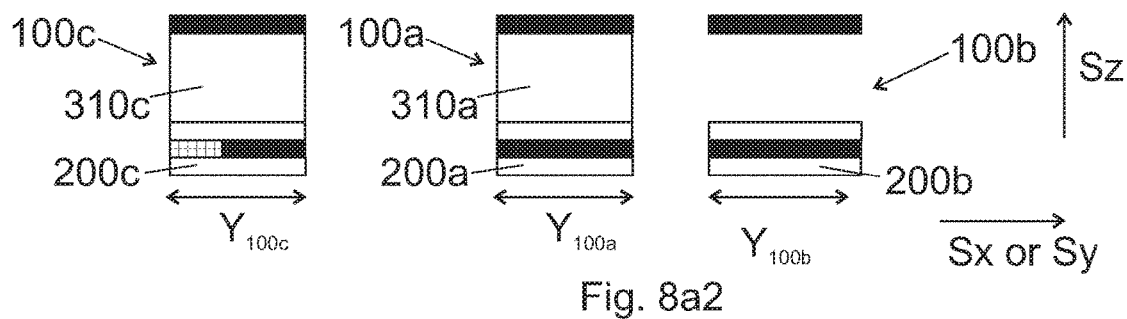
Fig. 8a2

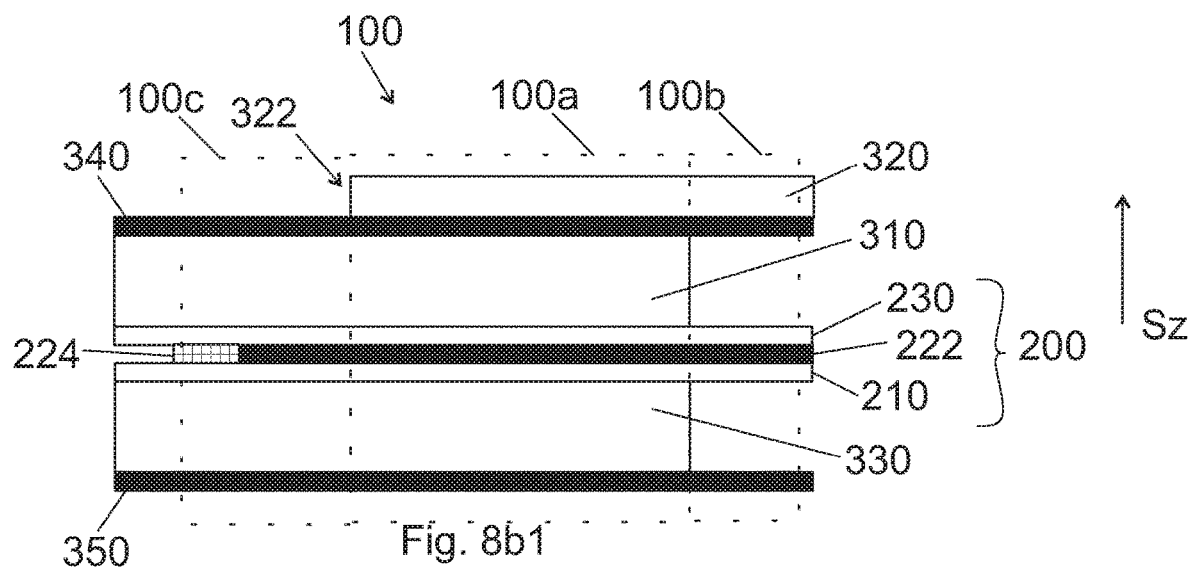
Fig. 8b1
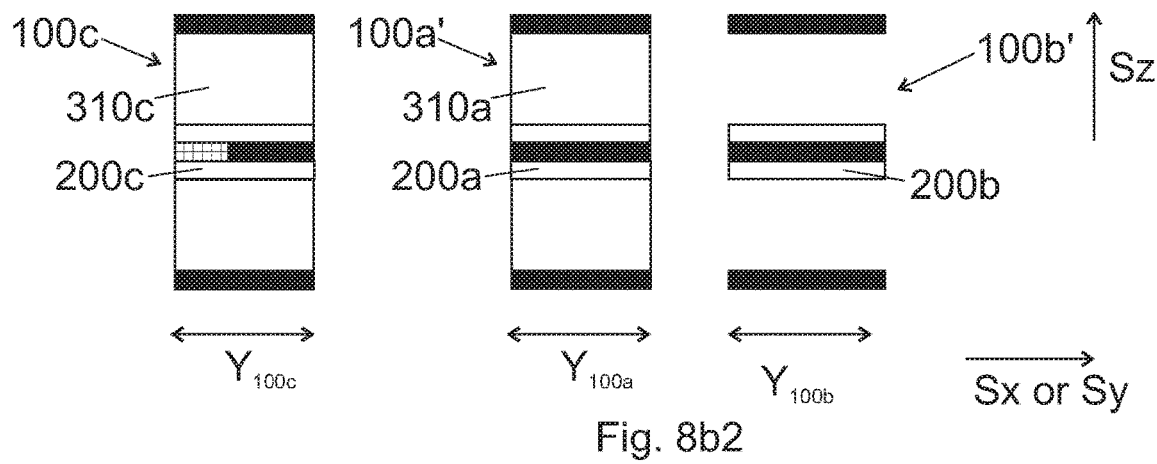
Fig. 8b2
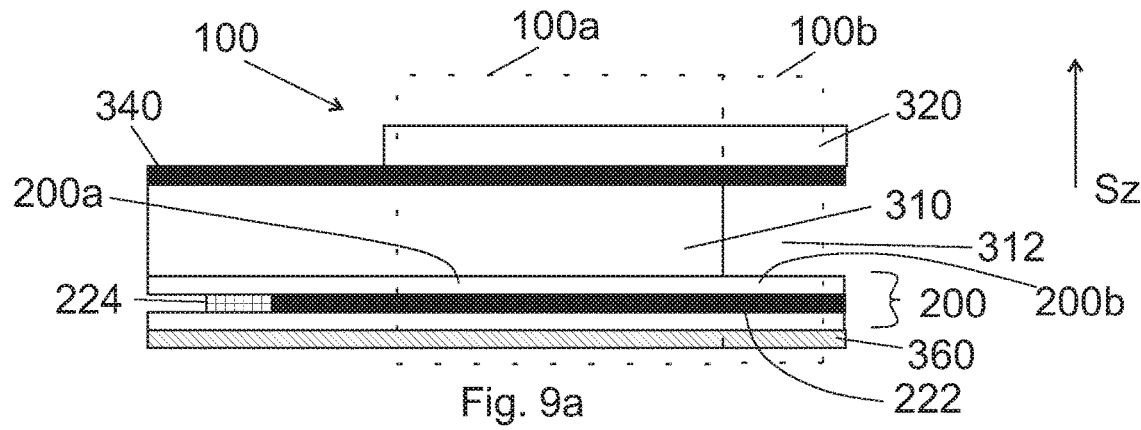
Fig. 9a

CAPACITIVE SENSOR

PRIORITY

This application claims priority of Finnish patent application number FI20185811 which was filed on 28 Sep. 2018, the contents of which are incorporated herein by reference.

TECHNICAL FIELD

The invention relates to force sensors, pressure sensors, and touch sensors. The invention relates to capacitive force sensors, capacitive pressure sensors, and capacitive touch sensors. The invention relates to wearable capacitive force, pressure, and touch sensors.

BACKGROUND

Interest in well-being has increased. This involves personal well-being as well as health care. This has resulted in many personal and medical monitoring devices, such as sensors. Such sensors can be embedded in clothing, such as gloves, mitts, footwear, helmets, etc. As for force or pressure sensors for garments, they may be e.g. piezo resistive, piezoelectric, or capacitive. Touch sensors, i.e. tactile sensors, are most often capacitive. A capacitive force/pressure/touch sensor typically involves only easily available materials. As an example, the patent FI 127245 discloses a capacitive force and/or pressure sensor. As opposed to a force and/or pressure sensor, a touch sensor needs not to have deformable material near an electrode.

Referring to FIG. 1, such sensors typically comprise a microelectronic chip 910, which is a rigid component. The microelectronic chip 910 comprises input/output channels 912a, 912b, such as bumps. These input/output channels 912a, 912b are located close to each other in order to have many input/output channels 912a, 912b for the chip 910 for better functionality.

Particularly in wearable sensors, the comfort of use is preferred. Therefore, a large part of the sensor may be formed on conformable sheet 930. The conformable sheet 930 may include wiring 932 that is also conformable and electrically conductive. Such wiring 932 may be made e.g. by printing. However, because of manufacturing techniques, the line width of the conformable wiring 932 is typically much larger than required by the distances between the input/output channels 912a, 912b of the microelectronic chip 910.

In order to electrically join the conformable wiring 932 to the input/output channels 912a, 912b, a flexible circuit board 920 may be used in between the microelectronic chip 910 and the conformable sheet 930. A flexible circuit board 920 can be manufactured with much smaller line width that a conformable wiring 932. Thus, the wiring 922 on the flexible circuit board can be made, at a first location, sufficiently narrow so as to contact the input/output channels 912a, 912b; and at a second location, the wires of the wiring 922 can be separated from each other so as to contact the wires of the conformable wiring 932.

However, such a solution is often mechanically unreliable. In particular, when used in such a way that the shape of the conformable part 930 and/or flexible part 920 changes, reliability problems are often encountered.

SUMMARY

The present invention relates to a capacitive sensor having a conformable section and a flexible section. In particular, the invention relates to a capacitive sensor, wherein the conformable section is attachable to the flexible section in such a way that the reliability of the attachment is high also in a mechanically changing environment. The reliability is improved by utilizing the stretchability of the electric wiring. The stretchability can be utilized primarily by making the sensor more resilient near a joint for connecting e.g. to a flexible board. The invention is disclosed in more specific terms in the independent claim 1. Some ways to improve stretchability are disclosed in claim 2. The stretchability can be utilized secondarily by connecting a wire, in a direction of thickness of the sensor, at a first point, to a reinforcement structure; and by not connecting the wire, in the direction of thickness of the sensor, at a second point, to the reinforcement structure, wherein the reinforcement structure extends from the first point to the second point. The embodiment is disclosed in more specific terms in the dependent claim 3. The stretchability of some parts of the sensor is disclosed more specifically in dependent claim 4.

BRIEF DESCRIPTION OF THE DRAWINGS

In the figures, the direction Sz denotes a direction of thickness of the sensor. The directions Sx and Sy are mutually perpendicular and perpendicular to Sz. The figures illustrate the sensor in substantially planar form, but since the sensor is conformable, it may be shaped to another form.

FIG. 3a1 shows in a side view a part of a capacitive sensor 100, FIG. 3a2 shows in a side view the part depicted in FIG. 3a1 divided to a first part 100a and a second part 100b, the first part and second parts shown by dotted lines, FIG. 3a3 shows in a side view in-plane elastic moduli of the parts of FIG. 3a2 after removal of reinforcement structure, FIG. 3a4 shows in a side view a part of a sensor as an alternative to the part shown in FIG. 3a1, FIG. 3b1 shows in a side view a part of a capacitive sensor 100, FIG. 3b2 shows in a side view the part depicted in FIG. 3b1 divided to a first part 100a and a second part 100b, the first part and second parts shown by dotted lines, FIG. 3b3 shows in a side view in-plane elastic moduli of the parts of FIG. 3b2 after removal of reinforcement structure, FIG. 3b4 shows in a side view a part of a sensor as an alternative to the part shown in FIG. 3b1, FIG. 3c1 shows in a side view a part of a capacitive sensor 100, FIG. 3c2 shows in a side view the part depicted in FIG. 3c1 divided to a first part 100a and a second part 100b, the first part and second parts shown by dotted lines, FIG. 3c3 shows in a side view in-plane elastic moduli of the parts of FIG. 3c2 after removal of reinforcement structure, FIG. 3d shows in a side view a part of a sensor divided to a first part 100a and a second part 100b, the first part and second parts shown by dotted lines, FIG. 3e1 shows in a side view a part of a sensor, wherein an adhesive forms a part of a compressible layer, FIG. 3e2 shows in a side view a part of a sensor, wherein a compressible material in a second part is thinner than in a first part, FIG. 6a shows in a top view a capacitive sensor 100, FIG. 6b shows in a side view a part of a capacitive sensor 100, FIG. 7 shows in a side view a capacitive sensor 100, FIG. 8a1 shows in side view a capacitive sensor 100, divided to a first part 100a, a second part 100b, and a third part 100c, the first, second, and third parts being shown by dotted lines, FIG. 8a2 shows in side view in a side view in-plane elastic moduli of the parts of FIG. 8a1, FIG. 8b1 shows in side view a capacitive sensor 100, divided to a first part 100a, a second part 100b, and a third part 100c, the first, second, and third parts being shown by dotted lines, FIG. 8b2 shows in side view in a side view in-plane elastic moduli of the parts of FIG. 8b1, FIGS. 9a to 9d show in side view parts of capacitive sensors 100.

DETAILED DESCRIPTION

Figure 1:
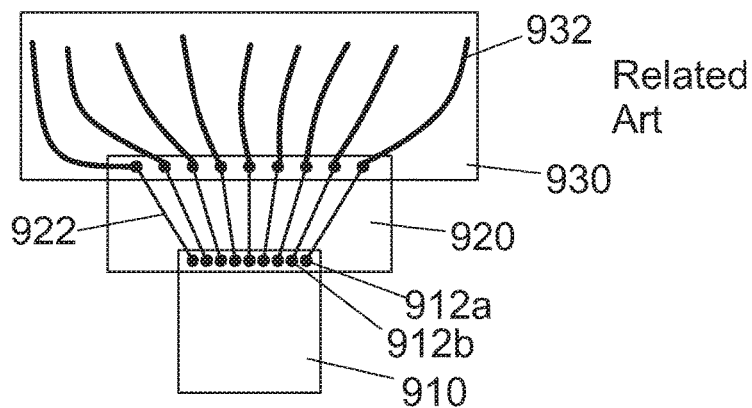
FIG. 1 shows schematically related art.

As indicated in background, the present invention relates to a capacitive sensor, e.g. a force and/or a pressure sensor or a touch sensor, with improved reliability under variable mechanical stress. Preferably, the sensor is conformable.

In capacitive sensors, the capacitance of an electrode is measured. The capacitance can be measured relative to surroundings or relative to another electrode, such a ground electrode. In general there are three working principles: (1) the dielectric material close to the electrode (e.g. in between two electrodes) changes, which changes the capacitance; and/or (2) the distance between two electrodes changes, which changes the capacitance in between these electrodes; and/or (3) an area of an electrode changes or a mutual area between two electrodes changes, which changes the capacitance of the electrode (e.g. relative to another electrode or surroundings). The mutual area may change e.g. under shear load. These principles are known to a skilled person. In a simple form, a capacitance of an electrode relative to its surroundings changes, when an object is moved close to or away from the electrode. Typically two electrodes are used for improved accuracy in such a way that material in between the electrodes is compressed in use. Such sensors are disclosed in the patent FI 127245. In touch sensors, the touching object (e.g. finger of a user) has a different dielectric constant than e.g. air. Thus, a capacitance of an electrode changes by movement of the touching object (according to the working principle 1 above).

Typically in force and/or pressure sensors, an elastic material near the measuring electrode, e.g. in between two electrodes, is compressed and deformed at least locally depending on the pressure applied (locally). The second electrode is not necessarily needed, since typically the object forming the pressure has a different dielectric constant than the compressed elastic material, whereby already the deformation causes a change of the capacitance relative to surroundings. Thus, a local pressure near an electrode can be determined. Moreover, when multiple electrodes are used at different locations, multiple local pressures can be determined at different locations. Force is an integral of the pressure. Therefore, in order to measure a force, substantially all the measurement area should be covered by the electrodes used for measurements, as described in the aforementioned patent. Therefore, in a force sensor, substantially all the measurement area should be covered by the electrodes used for measurements, while in a pressure sensor it suffices to provide electrodes used for measurements only to such areas, where the pressure is to be measured.

As indicated in the background, in order to be widely applicable on bodies with various shapes, the sensor, or at least most of the sensor, should be conformable. Conformable sensors are also usable in such environments, wherein their shape is subject to change, such as wearable electronics.

Herein the term conformable refers to material that is at least flexible and stretchable and preferably also compressible. As for the term flexible, a planar flexible material can be bent to a radius of curvature of 10 mm (or less) without breaking the material at a temperature of 20° C. Moreover, the flexible material can be thereafter turned back to the planar form at a temperature of 20° C. without breaking the material; or it may spontaneously turn back to planar form without breaking. As for the term stretchable, a stretchable material can be stretched by at least 10% in a reversible manner. In particular, a layer of stretchable material can be stretched by at least 10% in a reversible manner in a direction that is perpendicular to the direction of thickness of the layer. The reversibility of the stretching is spontaneous, i.e. elastic. As for the term compressible, a compressible material can be compressed by at least 10% in a reversible manner. In particular, a layer of compressible material can be compressed by at least 10% in a reversible manner in the direction of thickness of the layer. The reversibility of the compression is spontaneous, i.e. elastic. In this way, a planar conformable material is flexible as indicated above and stretchable in a direction of the plane of the planar conformable material; and preferably also compressible in the direction of its thickness as detailed above. A planar conformable material can be arranged to conform a surface of a hemisphere of a sphere having a radius of 10 cm (or less) at a temperature of 20° C. without breaking. Typically, a planar conformable material can be arranged to conform a surface of a hemisphere having a radius of 10 cm (or less) at a temperature of 20° C. without introducing significant plastic (i.e. irreversible) deformations to the material. Herein the term "significant" means that, when arranged on the hemisphere, the elastic strain of the conformable material is greater than the plastic strain thereof. Thus, a planar conformable material can be arranged to conform e.g. a surface of a foot or a fist.

Figure 2A:
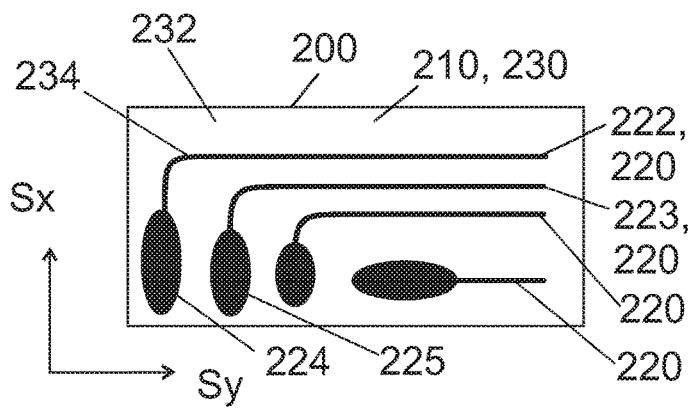
FIG. 2a shows in a top view a multilayer conductor structure.
Figure 2B:
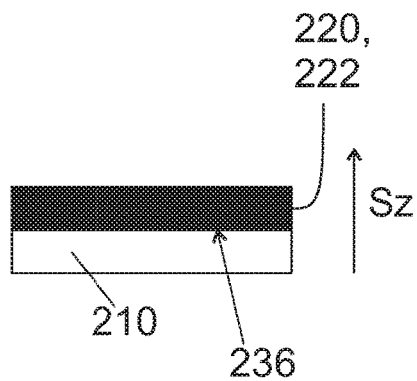
FIG. 2b shows in a side view such a part of a multilayer conductor structure that comprises wiring, which includes a first wire.
Figure 2C:
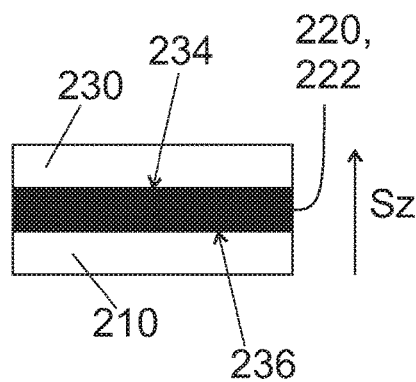
FIG. 2c shows in a side view such a part of another multilayer conductor structure that comprises wiring, which includes a first wire.
Figure 2D:
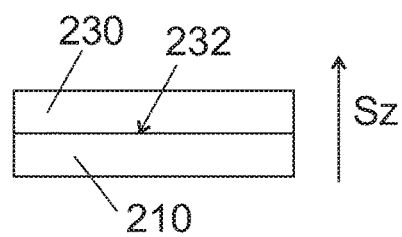
FIG. 2d shows in a side view such a part of a multilayer conductor structure that does not comprise a wire.

FIGS. 2a to 2d show parts of some sensors. FIG. 2a is a top view, while FIGS. 2b to 2d are side views, as indicated by the directions Sx, Sy, Sz in the figures. Sz refers to a direction of thickness of the sensor 100. The directions Sx, Sy, and Sz are mutually perpendicular and may depend on location, at least when the sensor is not planar. As conventional, the term "thickness" refers to a direction, in which the sensor extends the least. Thus, a thickness is smaller than a length or a width. Referring to FIGS. 2a to 2c, the sensor 100 comprises electrically conductive wiring 220, which comprises a first electrically conductive wire 222. The sensor 100 comprises a first electrode 224 for measuring a capacitance and coupled to the first electrically conductive wire 222. The function of the wire 222 is to couple the electrode 224 to a measuring circuit, e.g. via a flexible structure. Therefore, a first joint 226 is joined to the first wire 222, as indicated e.g. in FIG. 3a1. The joint 226 is suitable for joining the wire 222 to other electronics. The electrode 224 may form a part of the wiring 220. The wiring 220, in particular the first wire 222 thereof, is flexible and stretchable in the meaning discussed above for these terms. Preferably also the first electrode 224 is flexible and stretchable in the meaning discussed above for these terms. As will be detailed below, the wiring 220 may be arranged as a part of an electrically conductive multilayer structure 200.

Referring to FIGS. 3a1 to 3f, the sensor 100 comprises a first electrically conductive wire 222. The first electrically conductive wire 222 is flexible and stretchable in the meaning discussed above for these terms. The first electrically conductive wire 222 forms at least a part of wiring 220 (see FIG. 2a). The wiring 220 and/or the wire 222 may be manufactured e.g. by using such additive manufacturing techniques that produce stretchable conductive wirings, such as printing. In the alternative, the wiring may be laminated onto a layer of material. The wiring 220 may be manufactured (e.g. printed or laminated) onto a flexible and stretchable substrate 210. In the alternative, the wiring 220 may be manufactured (e.g. printed or laminated) onto a compressible layer 310.

Referring to FIGS. 3a1 to 3f, the sensor 100 comprises a compressible layer 310. In force and/or pressure sensors, the compressible layer 310 is configured to be compressed and deform under pressure in use. Moreover, because of the capacitive operational principle, the compressible layer 310 is also electrically insulating. Other properties and suitable materials for the layer 310 are discussed below. When the sensor 100 is used as a touch sensor (i.e. tactile sensor), a compressible layer 310 is not needed near the electrodes (224, 225). However, also in touch sensors, the compressible layer 310 may be used to improve reliability. Therefore, the compressible layer 310 needs not to extend so as to overlap with the first electrode 224.

Referring to FIGS. 3a1 to 3f, the sensor 100 comprises a reinforcement structure 320, such as a reinforcement layer. A function of the reinforcement structure 320 is to connect the first part 100a of the sensor 100 to the electronic part of the sensor, in particular a flexible board 410. Thus, a function of the reinforcement structure 320 is prevent too large in-plane stretching of the second part 100b of the sensor in between the first part 100a and the joint 226. In this way, a function of the reinforcement structure 320 is to reinforce the sensor 100 at least near a connection of the first wire 222 to other electronics of the sensor 100. In order to properly reinforce, the reinforcement structure 320 is integral, i.e. not constituted from separate parts. Thus the reinforcement structure 320 extends between each two points of the reinforcement structure 320. In particular, a first part 320a of the reinforcement structure 320 extends to a second part 320b of the reinforcement structure 320 (these parts are to be defined later). These parts (320a, 320b) are connected directly or via another part of the reinforcement structure 320. Moreover, preferably, no material interface is arranged in between the first part 320a and the second part 320b. The first electrically conductive wire 222 and the compressible layer 310 are arranged on a same side of the reinforcement structure 320. Correspondingly, a part of the reinforcing structure 320 is not arranged in between the first electrically conductive wire 222 and the compressible layer 310 in the direction Sz of thickness of the sensor 100. Preferably, a part of the compressible layer 310 is arranged in between the first electrically conductive wire 222 and the reinforcement structure 320 in the direction Sz. However, as indicated in FIG. 3d, a part of the first electrically conductive wire 222 may be arranged in between the compressible layer 310 and the reinforcement structure 320. The reinforcement structure 320 may be or comprise a layer of suitable reinforcing material. The reinforcement structure 320 may be or form a part of packaging for a rigid component 420 and/or flexible board 410 of the sensor 100, as in FIG. 3f. The reinforcement structure 320 may be electrically conductive, whereby it may be used as a ground electrode, in a similar manner as a common potential electrode 340. The reinforcement structure 320 may be a top layer, and can be finished according to needs. Thus, the reinforcement structure may be used as a top layer 380.

It has been noticed that the stretchability of the first wire 222 can be utilized to improve the reliability of the sensor 100. In particular, since the first wire 222 is stretchable, its ability to stretch may be utilized to improve reliability. This property can be utilized such that, in use, a part of the first wire 222 (i.e. the part of the wire 222 within a second part 100b of the sensor as will be discussed below) takes in most of the mechanical deformations. This can be achieved by material design in such a way that near a joint 226 the sensor 100, except for the reinforcement structure 320, deforms in-plane more easily than farther away from the joint 226. The joint 226 is connected to the first wire 222, and via the first wire 222 to a first electrode 224.

More specifically and with reference to FIGS. 3a2, 3b2, and 3e2, the resilience of the sensor 100, except for the reinforcement structure, near the joint 226 the sensor 100 can be improved at least by three solutions:

(i) the second part 100b of the sensor 100 comprises a second part 310b of the compressible layer 310, as indicated in FIGS. 3a1 and 3a2; and a Young's modulus of the second part 310b of the compressible layer 310 is less than a Young's modulus of the first part 310a of the compressible layer 310 or (ii) the compressible layer 310 does not extend to the second part 100b of the sensor 100, as indicated in FIG. 3b2 or (iii) the thickness $T_{310b}$ of a second part 310b of the compressible layer 310 is less than a thickness $T_{310a}$ of a first part 310a of the compressible layer 310, as indicated in FIGS. 3e1 and 3e2.

As will be detailed below, by utilizing at least one of these solutions, the resilience of a second part 100b of the sensor 100 is improved. In particular, each one of the alternatives (i) and (iii) has the technical effect that an in-plane stiffness of the second part 310b of the compressible layer 310 is less than an in-plane stiffness of the first part 310a of the compressible layer 310. Herein the in-plane stiffness of the part 310a, 310b refers to the in-plane elastic modulus of that part as multiplied by the thickness of that part. In this description, the in-plane elastic modulus is considered equivalent to an in-plane Young's modulus, a term also commonly used for this property.

As for the alternative (ii), since the compressible layer 310 does not extend to the second part 100b, a gap 312 is left next to the first part 310a of the compressible layer, and, effectively, an in-plane stiffness of a gap is zero. Thus, all the alternatives (i)-(iii) aim at decreasing the in-plane stiffness of the compressible layer within the second part 100b. Moreover, at least a part of the second part 100b is arranged in between the joint 226 and the first part 100a. Herein the term "in between" refers to being in between in a direction that is perpendicular to the direction Sz of thickness of the sensor.

However, the other layers of the structure may also affect the resilience. It has been found that the reliability is further improved, when the sensor has a modified first part 100a' with a first in-plane stiffness and a modified second part 100b' with a second in-plane stiffness that is lower than the first in-plane stiffness, wherein the modified first part 100a' has been modified from the first part 100a of the sensor 100 by removing the first part 320a of the reinforcement structure 320 and the modified second part 100b' has been modified from the second part 100b of the sensor 100 by removing the second part 320b of the reinforcement structure 320. The in-plane stiffness refers to an in-plane elastic modulus ($Y_{100a}$, $Y_{100b}$) multiplied by a thickness of the layer. The modified first (100a' and second (100b') parts and the corresponding in-plane elastic moduli are shown in FIGS. 3a3, 3b3, and 3c3. Also here, at least a part of the second part 100b is arranged in between the joint 226 and the first part 100a in a direction that is perpendicular to the direction Sz of thickness of the sensor. In addition, preferably, the whole area in between the joint 226 and the first part 100a is more resilient than the first part 100a. More precisely, in an embodiment, the sensor 100 does not have such a part, (i) which is arranged in between the joint 226 and the first part 100a, and (ii) of which in-plane stiffness (e.g. elastic modulus) is equal to or greater than the first in-plane stiffness (e.g. elastic modulus $Y_{100a}$) after removal of the reinforcement structure 320. More preferably, the sensor 100 does not have such a part, (i) which is arranged in between the joint 226 and the first part 100a, and (ii) of which in-plane stiffness (e.g. elastic modulus), after removal of the reinforcement structure 320, is higher than the second in-plane stiffness (e.g. elastic modulus $Y_{100b}$). In an embodiment, the second part 100b of the sensor extends to the joint 226 from a common edge 100ab of the first part 100a and the second part 100b.

Figure 4A:
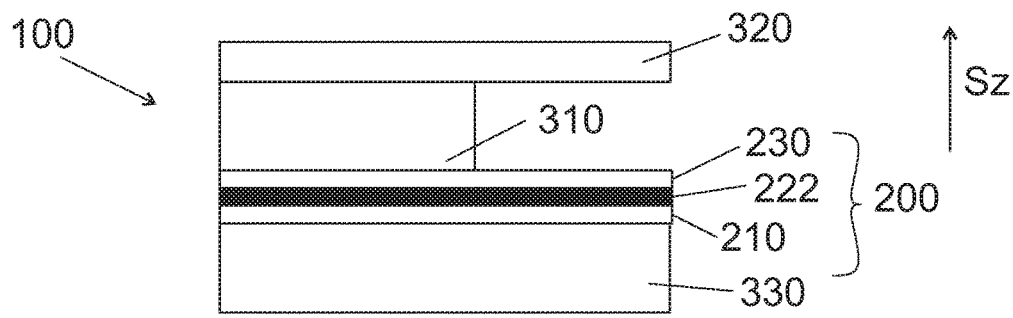
FIG. 4a shows in a side view a part of a capacitive sensor 100.
Figure 4B:
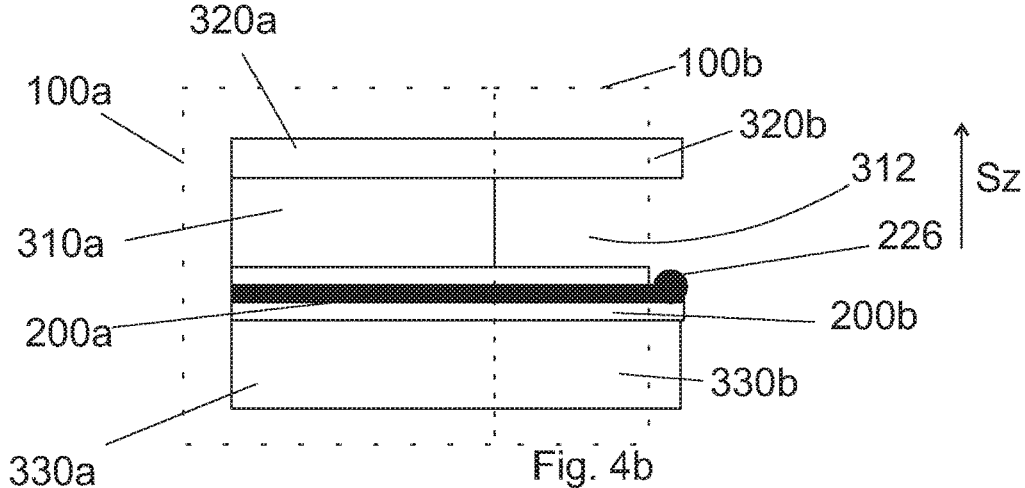
FIG. 4b shows in a side view the part depicted in FIG. 4a divided to a first part 100a and a second part 100b, the first part and second parts shown by dotted lines.
Figure 4C:
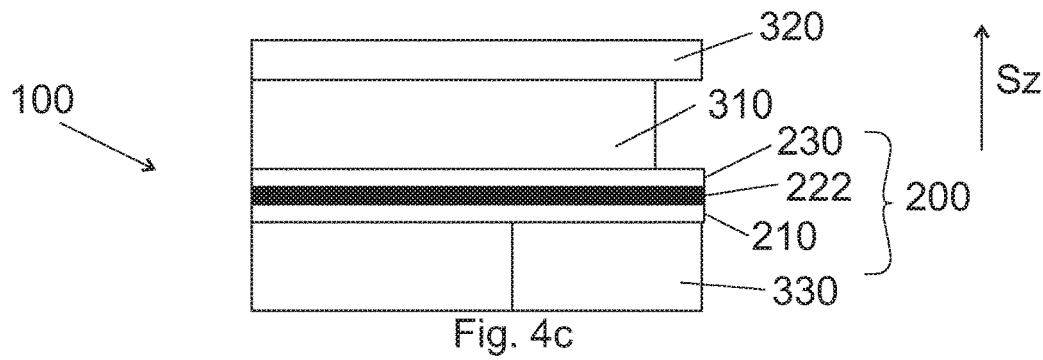
FIG. 4c shows in a side view a part of a capacitive sensor 100.
Figure 3F:
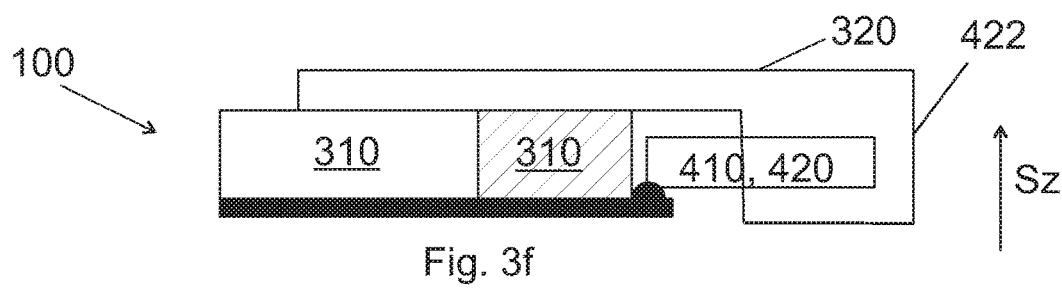
FIG. 3f shows in a side view a sensor, wherein package of the electronics forms a reinforcement structure.
Figure 4D:
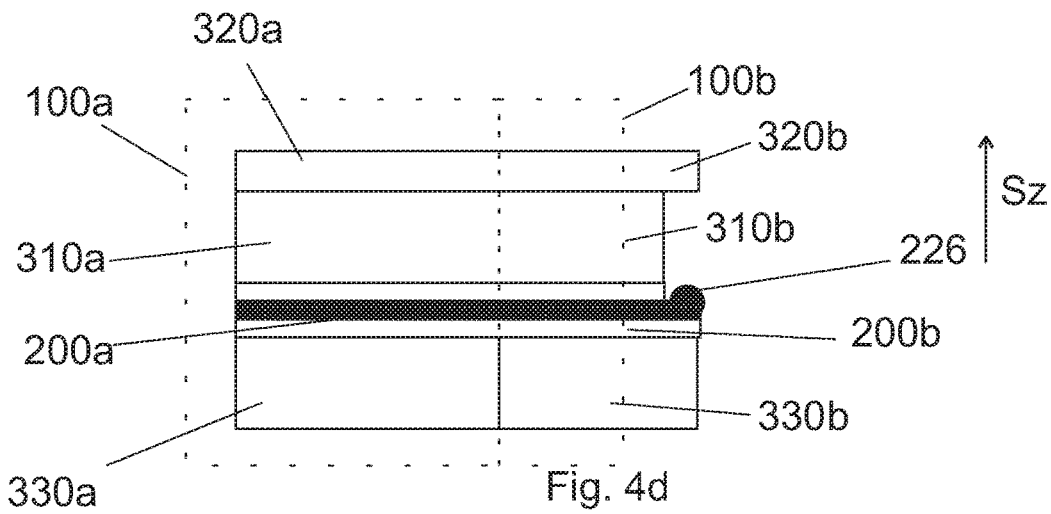
FIG. 4d shows in a side view the part depicted in FIG. 4c divided to a first part 100a and a second part 100b, the first part and second parts shown by dotted lines.

With reference to FIGS. 3a1 to 3f, the capacitive sensor 100 has a first part 100a of the capacitive sensor 100 and a second part 100b of the capacitive sensor 100. Thus, the sensor is dividable to the parts 100a, 100b. Such a division of the sensor 100 is shown e.g. in FIGS. 3a1 to 3d and 4a to 4d by the dotted rectangles. The first part 100a extends through the sensor 100 in the direction Sz of thickness of the sensor 100. The second part 100b extends through the sensor 100 in the direction Sz of thickness of the sensor. FIG. 3a2 shows the division of the sensor of FIG. 3a1, FIG. 3b2 shows the division of the sensor of FIG. 3b1, FIG. 3c2 shows the division of the sensor of FIG. 3c1, FIG. 4b shows the division of the sensor of FIG. 4a, and FIG. 4d shows the division of the sensor of FIG. 4c to these two parts. As indicated in FIGS. 8a1 to 8b2, the sensor can be divided to more than two parts. The division is to be understood as a mental process of defining such parts; the physical sensor 100 is not physically divided. The first part 100a of the sensor 100 and the second part 100b of the sensor 100 are defined so that they share a common edge 100ab, as shown in the FIGS. 3a2, 3b2, 3c2, and 12.

The first part 100a of the sensor 100 comprises a first part 320a of the reinforcement structure 320 (as discussed above), a first part 222a of the first electrically conductive wire 222, and a first part of 310a the compressible layer 310. These layers are arranged relative to each other in such a way that the first part 320a of the reinforcement structure 320 overlaps, in the direction Sz of thickness of the sensor 100, with the first part 222a of the first electrically conductive wire 222, or at least a region reasonable close to the first part 222a of the first electrically conductive wire 222. Thus, the compressible layer 310 transmits the supportive force of the reinforcement structure 320 to the first electrically conductive wire 222 within the first part 100a. For example, the reinforcement structure 320 may be provided with an aperture such that the aperture overlaps the first part 222a of the first electrically conductive wire 222. In a preferable embodiment, within the first part 100a, the first part 320a of the reinforcement structure 320 radially surrounds such a straight line that is parallel to the direction Sz of thickness at the location of first part 222a of the first wire 222 and penetrates the first part 222a of first wire 222.

Moreover, the first part 320a of the reinforcement structure overlaps, in the direction Sz of thickness of the sensor 100, with the first part 310a of the compressible layer 310 (or at least part thereof). Throughout this description the term overlap refers to parts of layers being arranged, in the direction of the thickness Sz of the sensor 100, on top of each other. As indicated e.g. in FIG. 3b2, the first part 222a of the first electrically conductive wire 222 may be comprised by a first part 200a of a multilayer conductor structure 200. In such a case, preferably, the first part 320a of the reinforcement structure 320 overlaps, in the direction Sz of thickness of the sensor 100, with the first part 200a of the multilayer conductor structure 200. Moreover, at least a part of the first part 310a of the compressible layer 310 overlaps with at least a part of the first part 222a the first electrically conductive wire 222 in the direction Sz of thickness of the sensor 100. Typically, a part of the first part 310a of the compressible layer 310 overlaps with the first part 222a the first electrically conductive wire 222 in the direction Sz of thickness of the sensor 100.

The second part 100b of the capacitive sensor 100 comprises a second part 320b of the reinforcement structure 320 and a second part 222b of the first electrically conductive wire 222. These layers may be arranged relative to each other in such a way that the second part 320b of the reinforcement structure 320 overlaps with the second part 222b of the first electrically conductive wire 222 in the direction Sz of the thickness of the sensor 100, or is at least close to the second part 222b. In a preferable embodiment, within the second part 100b, the second part 320b of the reinforcement structure 320 radially surrounds such a straight line that is parallel to the direction Sz of thickness at the location of second part 222b of the first wire 222 and penetrates the second part 222b of first wire 222. As indicated e.g. in FIG. 3b2, the second part 222b of the first electrically conductive wire 222 may be comprised by a second part 200b of a multilayer conductor structure 200.

As indicated above, in an embodiment, a modified first part 100a' of the sensor 100, the modified first part 100a' including all other parts of the sensor 100 than the reinforcement structure 320, has a first in-plane elastic modulus $Y_{100a}$. The term in-plane elastic modulus refers e.g. to Young's modulus as measured in a test, wherein a direction of the deformation is perpendicular to the direction Sz of thickness of the sensor 100. In such a case, the direction of the deformation is parallel to a linear combination of the perpendicular directions Sx and Sy (including Sx and Sy as such). In case the sensor 100 is planar, the direction of the deformation is in plane of the sensor 100. Moreover, in such an embodiment, a modified second part 100b' of the sensor 100, the modified second part 100b' including all other parts of the sensor 100 than the reinforcement structure 320, has a second in-plane elastic modulus $Y_{100b}$. In an embodiment, the second in-plane elastic modulus $Y_{100b}$ is smaller than the first in-plane elastic modulus $Y_{100a}$. The first and second elastic moduli $Y_{100a}$ and $Y_{100b}$ are indicated in FIGS. 3a3, 3b3, and 3c3. Referring in particular to FIGS. 3a3 and 3c3, the second elastic modulus $Y_{100b}$ is smaller, because in those embodiments, within the second part 100b of the sensor, the material of the second part 310b of the compressible layer 310 is softer than the material within the first part 100a of the sensor, i.e. the material of the first part 310a of the compressible layer. Referring in particular to FIG. 3b3, the second elastic modulus may be greater, because the second part 100b does not comprise a part of the compressible layer 310. However, in such a case, the in-plane stiffness of the modified second part 100b' is less the in-plane stiffness of the modified first part 100a', as discussed above. Moreover, in FIG. 3b2, a gap 312 is formed in between the second part 222b of the wire 222 and the second part 320b of the reinforcement structure 320. The resilience (or stiffness) is given in terms of the modified parts 100a' and 100b', since it has been noticed that the reinforcement structure 320 can be engineered according to needs also locally (i.e. separately in both the parts 100a and 100b) without significantly affecting the reliability.

The material of the second part 310b of the compressible layer 310 (if present) may have a lower Young's modulus than the material of the first part 310a of the compressible layer 310, e.g. at least 25% lower. In case a gap 312 is used instead of the material of the second part 310b, the modulus of the gap is undefined, and practically zero.

With reference to FIG. 3e2, the in-plane stiffness may be affected in addition or alternatively by the thickness of the layer(s). As indicated in FIG. 3e2, within the first part 100a, the compressible layer 310 may be thicker than within the second part 100b, whereby a gap 312, of which height is less than the thickness of the layer 310, is left next to the compressible layer 310. Therefore, the in-plane stiffness of the modified first part 100a' of the sensor 100 is more than that of the modified second part 100b' of the sensor 100, because the compressible layer 310 is thinner within the second part 100b. This happens, even if the materials of the first 310a and second 310b parts of the compressible layer are the same. The thickness of the first part 310a of the compressible layer is denoted by $T_{310a}$ and the thickness of the second part 310b of the compressible layer is denoted by $T_{310b}$. In FIG. 3e1, the layer 310 is thinner in the second part 100b because of lack of an adhesive 314, which is present in the first part 100a and forms a part of the compressible layer 310. The thickness $T_{310b}$ of the second part 310b may be e.g. at most 98% of the thickness $T_{310a}$ of the first part 310a in particular if adhesive 314 is used to thicken the layer 310 only in the first part 100a. In such a case an adhesive 314 is typically stiffer than the rest of compressible layer.

FIGS. 2a to 2d show a parts of sensors, wherein the wiring 220 is arranged as a part of an electrically conductive multilayer structure 200.

Referring to FIG. 2b, in an embodiment, the sensor 100 comprises a multilayer conductor structure 200, which comprises the wiring 220 including the first electrically conductive wire 222. The multilayer conductor structure 200 comprises a flexible and stretchable substrate 210. The substrate is thus flexible and stretchable in the meaning discussed above for these terms. Preferably, the flexible and stretchable substrate 210 is also compressible, whereby it is preferably conformable. The wiring 220, in particular the first electrically conductive wire 222, is arranged on the substrate 210. Therefore, the flexible and stretchable substrate 210 forms an interface 236 with the first electrically conductive wire 222. With reference to FIG. 3a4, the substrate 210 can be used to protect the wiring 220 (and the wire 222), at least when the multilayer conductor structure 200 comprises only the wiring and the substrate 210. Having at least the substrate 210 such that it forms the interface 236 with the first electrically conductive wire 222 improves the reliability of the structure, since in such a case, the wire 222 is attached, on at least one side, to a resilient layer 210 (see FIG. 2b).

Referring to FIG. 2c, more preferably, the multilayer conductor structure 200 further comprises a flexible and stretchable protective layer 230. The protective layer 230 may further protect at least a part of the wiring 220. Moreover, in other parts, the protective layer 230 is attached to the substrate 210. Thus, the wiring 220 is arranged in between the flexible and stretchable substrate 210 and flexible and stretchable protective layer 230. In an embodiment, at least a part of the first electrically conductive wire 222 is arranged in between the flexible and stretchable substrate 210 and the flexible and stretchable protective layer 230. Being so arranged, at such locations that the wiring does not exists, the protective layer 230 forms a first interface 232 with the flexible and stretchable substrate 210 (see FIG. 2d). Correspondingly, at such locations that the wiring 220 exists, the protective layer 230 forms a second interface 234 with the first electrically conductive wire 222 (FIG. 2c). Having also the protective layer 230 such that it forms the interface 234 with the first electrically conductive wire 222 further improves the reliability of the structure, since in such a case, the wire 222 is attached, on both sides, to resilient layers 210, 230 (see FIG. 2c).

In such an embodiment, where the first electrode 224 forms a part of the wiring 220, at least a part of the first electrode 224 is arranged on the same side of the flexible and stretchable substrate 210 as the wiring 220. In such a case, preferably the (whole) first electrode 224 is arranged on the same side of the flexible and stretchable substrate 210 as the wiring 220. In case also a protective layer 230 is used and the first electrode 224 forms a part of the wiring 220, at least a part of the first electrode 224 is arranged in between the flexible and stretchable substrate 210 and the flexible and stretchable protective layer 230. In such a case, preferably the (whole) first electrode 224 is arranged in between the flexible and stretchable substrate 210 and the flexible and stretchable protective layer 230.

Preferably the multilayer conductor structure 200 consists of the flexible and stretchable substrate 210, the flexible and stretchable protective layer 230, and the layer or layers in between the flexible and stretchable substrate 210 and the flexible and stretchable protective layer 230. As indicated above, in an embodiment, at least a part of the wiring 220 is arranged in between the flexible and stretchable substrate 210 and the flexible and stretchable protective layer 230.

However, some adhesive may also be arranged in between the flexible and stretchable substrate 210 and the flexible and stretchable protective layer 230 in order to join the layers together.

Preferably, the sensor 100 comprises multiple electrodes, such as the first electrode 224 and a second electrode 225 (see FIG. 2a). FIG. 2a shows also other electrodes, even if they do not have their own reference numbers for clarity. Preferably the electrodes are arranged in such a way that a capacitance is measurable using all electrodes simultaneously. In contrast, in some prior art applications multiplexing is used, whereby only some of the electrodes can be used at a time to measure the capacitance. In particular, in an embodiment, the electrodes cover most of the cross-sectional area of the sensor, such as at least 50% or at least 80% of the cross-sectional area, and the capacitance is measurable using all electrodes simultaneously over the whole cross-sectional area covered by the electrodes.

Thus, in an embodiment, the electrode 224 (or the electrodes 224, 225) define measurement areas. A measurement area is a part of the sensor 100 extending through the sensor 100 in the direction Sz of thickness. Within a measurement area, at least one electrode 224 (or 225) is arranged. The measurement area defined by the electrode is the area, from which capacitance is configured to be measured by the electrode. Moreover, electrodes of two different measurement areas are not an a galvanic contact with each other. Furthermore, a rigid component 420 of the sensor 100 may be configured to measure a capacitance of each one of the measurement areas using the electrodes, of which each electrode define one, and only one, of the measurement areas. Preferably, the rigid component 420 is configured to measure the capacitance from the whole area of the first electrode 224 at one instance of time. In other words, preferably, subsequent measurements are not performed to measure the capacitance from the whole area of the first electrode 224. This has the beneficial effect that since multiplexing needs not be used, the temporal accuracy of the measurement can be improved. More preferably, for each measurement area, the sensor comprises a wire 222, 223 that is attached in an electrically conductive manner to an electrode 224, 225. This has the beneficial effect that a capacitance is measurable from each measurement area simultaneously. Preferably, the first wire 222 is electrically connected to only one electrode 224. More preferably, each wire 222, 223, is electrically connected to only one electrode (224, 225, respectively).

In addition to the extent of the compressible layer 310 or the material selections of its parts 310a, 310b, it has been noticed that the reliability can be further improved by attaching, within the first part 100a of the sensor 100, the first wire 222, optionally via other layer(s), to the reinforcement structure 320 in the direction Sz of thickness of the sensor. Attaching in the direction Sz of thickness of the sensor does not mean that the reinforcement structure 320 needs to overlap with the first part 222a of the wire 222, e.g. when a layer of material is arranged in between the first part 222a of the wire 222 and the reinforcement structure 320. Referring to FIG. 3a2, the first part 222a of the wire 222 is attached (in the direction Sz) to the first part 310a of the compressible layer 310, which is attached (in the direction Sz) to the first part 320a of the reinforcing structure 320a. This may be done, even if the reinforcement structure 320 does not overlap with the wire 222, e.g. the reinforcement structure 320 is provided with an aperture that overlaps with the wire 222. By attaching the first part 222a of the wire to the reinforcing structure 320, the reinforcing structure 320 strengthens the structure for improved reliability.

Furthermore, the reliability can be improved by not attaching, within the second part 100b of the sensor 100, the second part 222b of the wire 222 to the second part 320b of the reinforcing structure 320 in the direction Sz of thickness of the sensor 100; neither directly, nor via other layer(s). Referring to FIG. 3a2, in such a case (i) the second part 222b of the wire 222 is not attached to the second part 310b of the compressible layer and/or (ii) the second part 310b of the compressible layer is not attached to the second part 320b of the reinforcement structure 320. By not attaching (within the second part 100b) the wire 222 to the reinforcement structure 320, the wire 222 is configured to move freely with respect to the reinforcement structure 320, which allows for the wire 222 to take in the mechanical strain.

In case the first electrically conductive wire 222 forms a part of the multilayer conductor structure 200, as discussed above, for manufacturing reasons, it may be feasible to not attach, within the second part 100b, the second part 200b of the multilayer conductor structure 200 to the second part 320b of the reinforcement structure 320, while the first electrically conductive wire 222 remains attached to the other layer 210 or layers 210, 230 of the multilayer conductor structure 200.

Therefore, in an embodiment, the first part 200a of the multilayer conductor structure (or the first part 222a of the wire 222, if neither of the layers 210, 230 is used) is attached to a neighboring layer 310, 320, 330; preferably to both neighboring layers if present; to improve reliability within the first part 100a of the sensor. Moreover, the neighboring layer is attached to the first part 320a of the reinforcement structure 320; unless the neighboring layer already is the reinforcement structure 320. In an embodiment, the second part 200b of the multilayer conductor structure is configured to move relatively freely with respect to the neighboring layer 310, 320, 330 to further improve reliability near a connection. As for the term "neighboring layer", this term refers to a layer that is next to the multilayer conductor structure 200. For example, in FIGS. 3a1 to 3a3, the compressible layer 310 forms a neighboring layer for the wire 222. For example, in FIGS. 3b1 to 3c3, the compressible layer 310 forms the neighboring layer for the multilayer conductor structure 200. In FIG. 3d, both the reinforcement layer 320 and the compressible layer 310 are neighboring layers, and either one can be considered as the neighboring layer. In FIGS. 4a to 4d, both the compressible layer 310 and a spacer layer 330 are neighboring layers, and either one can be considered as the neighboring layer. As for the term "move relatively freely" and the definition of the second part 100b, preferably, the whole second part 200b of the multilayer conductor structure is configured to move relatively freely with respect to the neighboring layer 310, 320, 330. Thus, in an embodiment, no part of the second part 222b of first electrically conductive wire 222 is attached, directly or via other layers, in the direction Sz of the thickness of the sensor 100, to the second part 320b of the reinforcement structure 320.

Within the first part 100a of the sensor, the first part 222a of the first wire 222 is attached to a neighboring layer or both neighboring layers in the direction of thickness Sz of the sensor 100; and further to the first part 320a of the reinforcement structure 320 (unless the first part 320a already is the neighboring layer). It may be attached using adhesive. This improves reliability within the first part 100a. Moreover, in an embodiment, the second part 222b of the wire 222 is not attached to second part 320b of the reinforcement structure 320 (if present). In its part, this allows for the free movement of the layers relative to each other.

As indicated above, the relatively free movement is achieved primarily by the extent of the compressible layer 310 or the material selections of its parts 310a, 310b; secondarily by not attaching the second part 222b of the first wire 222 to the second part 320b of the reinforcement structure 320; and tertiarily by the different in-plane elastic stiffnesses, defined by the product of the thickness and the in-plane modulus $Y_{100a}$, $Y_{100b}$ of the respective modified part 100a', 100b'.

Outside the reinforcing layer 320, the multilayer conductor structure 200, if used, is preferably attached to the neighboring layer (310, 330) to help handling and to improve reliability. If a multilayer conductor structure 200 is not used, outside the reinforcing layer 320, the first electrically conductive wire 222 is preferably attached to the neighboring layer (310, 330), which is adjacent to the wire 222, to help handling and to improve reliability.

To improve the reliability of the connection to other electronics, the first electrically conductive wire 222 is attached to a first joint 226 for connecting the first wire 222 to another electrically conductive structure 400. Such a joint 226 is shown e.g. in FIGS. 3a1, 3a2, 3b2, 3c2, 3d, 4b, 4d, 6b, and 12. Even if not shown, such a joint is present in also other embodiments. Such another electrically conductive structure 400 may be e.g. a flexible circuit board 410 or a connector 405. A connector 405 may be used to connect the wire 222 e.g. to a flexible board or a chip. Moreover, in order to use the first joint 226, the first wire 222, and the first electrode 224 for measurements, the first electrically conductive wire 222 extends from the first joint 226 via the second part 100b of the sensor 100 to the first part 100a of the sensor 100 and further to the first electrode 224. The first joint 226 may be arranged within the second part 100b of the sensor 100; or the first joint 226 may be arranged outside the first part 100a and outside the second part 100b. However, as indicated above, at least a part of the second part 100b is arranged in between the joint 226 and the first part 100a. Herein term "in between" refers to being in between in a direction (Sx, Sy, or their linear combination) that is perpendicular to the direction Sz of the thickness of the sensor 100. In a preferable embodiment, a part of the reinforcement structure 320 overlaps with the first joint 226. However, the reinforcement structure needs not to overlap the first joint 226. It suffices that the reinforcement structure 320 radially surrounds at least partly such a straight line that is parallel to the direction Sz of thickness at the location of the first joint 226 and penetrates the first joint 226. This further improves the reliability. In another preferable embodiment, a part of the reinforcement structure 320 overlaps with at least a part of the flexible circuit board 410. This further improves the reliability.

As for the capability of the second part 100b to improve reliability, the first wire 222 should extend within the second part 100b (e.g. in between the first joint 226 and the first part 100a) for a reasonable length. It has been found that preferably the first wire 222 extends within the second part 100b such a distance that is longer than a thickness $T_{310a}$ of the compressible layer 310 within the first part 100a. Thus, and with reference to FIGS. 3a2 and 3b2, preferably, a length $L_{222b}$ of the part 222b of the first wire 222 that extends within the second part 100b of the sensor 100 is greater than a thickness $T_{310a}$ of the compressible layer 310 within the first part 100a, i.e. $L_{222b} > T_{310a}$ (see FIGS. 3a2 and 3b2). In addition or alternatively, the length $L_{222b}$ may be e.g. at least 1 mm, at least 2 mm, or at least 5 mm. In case the first wire 222 meanders, the length $L_{222b}$ may be measured along the wire 222.

As indicated above, the multilayer conductor structure 200, if used, is flexible and stretchable; and preferably conformable. Moreover, the flexible and stretchable substrate 210, and, if used, also the flexible and stretchable protective layer 230 are electrically insulating. E.g. their electrical resistivities may be at least 10 Ωm at a temperature of 23° C. At least the following materials are suitable for the layers 210 and/or 230: polyurethane, polyethylene, poly (ethylene-vinyl acetate), polyvinyl chloride, polyborodimethylsiloxane, polystyrene, acrylonitrile-butadiene-styrene, styrene-butadienestyrene, ethylene propylene rubber, neoprene, cork, latex, natural rubber, silicone, and thermoplastic elastomeric gel. Either one or both of the layers 210, 230 may be selected from this group of materials.

As for the wiring 220, in an embodiment, the first wire 222 is made of such material that is stretchable by at least 10% without breaking. Moreover, in an embodiment, the first electrode 224 is made of such material that is stretchable by at least 10% without breaking. Such material may be e.g. ink, paste, or conductive polymer. In an embodiment, the first wire 222 (and optionally the first electrode 224) comprises some material having an electric conductivity of at least 1 S/m at a temperature of 23° C. In an embodiment, the first wire 222 (and optionally the first electrode 224) comprises electrically conductive particles, such as flakes or nanoparticles, attached to each other in an electrically conductive manner. In an embodiment, the first wire 222 (and optionally the first electrode 224) comprises electrically conductive particles of some material having an electric conductivity of at least 1 S/m at a temperature of 23° C. In an embodiment, the first wire 222 (and optionally the first electrode 224) comprises electrically conductive particles comprising at least one of carbon, zinc, nickel, platinum, iron, copper, silver, aluminium, and gold. In an embodiment, the first wire 222 (and optionally the first electrode 224) comprises electrically conductive polymer, such as polyaniline, a polyvinyl (e.g. polyvinyl alcohol or polyvinyl chloride), and/or PEDOT:PSS (i.e. poly(3,4-ethylenedioxythiophene) polystyrene sulfonate). In some electrically conductive polymers, the conductivity may be the result of electrically conductive particles as discussed above. What has been said about the material of the first wire 222 applies, in an embodiment, to the wiring 220 (i.e. all the wires 222, 223) and/or to all the electrodes (224, 225), optionally also to the common potential electrode(s) (340, 350).

Figure 11:
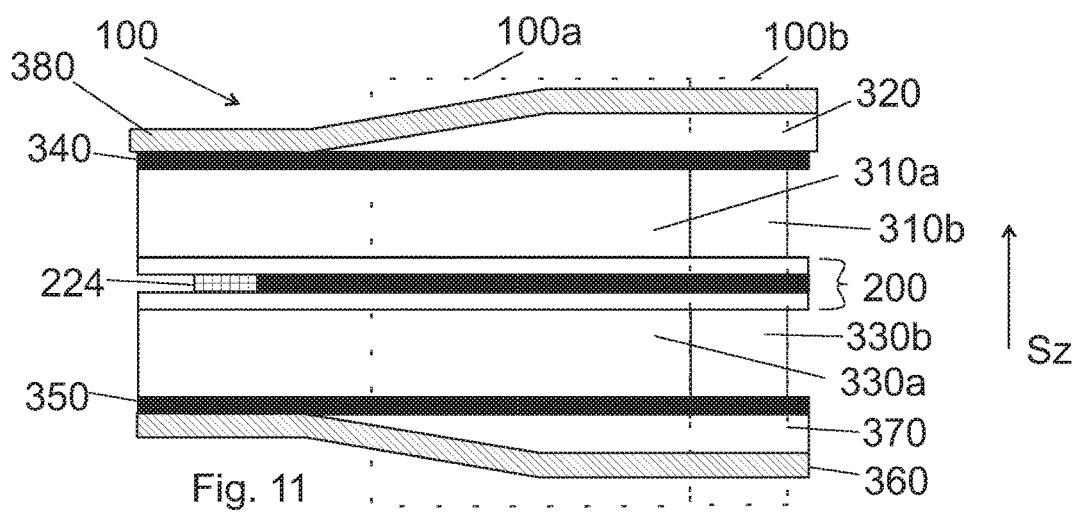
FIG. 11 shows in side view parts of a capacitive sensors 100.

The reinforcement structure 320 is a reinforcement in the sense that it has been observed to improve reliability. It needs not be hard or stiff. With reference to FIG. 3e1, in an embodiment, the reinforcement may comprise textile and/or a film. Thus, a top layer similar to a top layer 380 of FIG. 11 may serve as a reinforcement structure 320. However, as indicated in FIG. 11 the sensor may comprise both a top layer and a reinforcement structure. As indicated in FIG. 3e1, the compressible layer 310 may comprise a compressible body 310' and adhesive 314. The adhesive 314 may attach the compressible body 310' to the wire 222. The adhesive 314 furthermore thickens the compressible layer 310 and increases its in-plane stiffness. In FIG. 3e1, the first part 100a of the sensor 100 comprises the adhesive 314, and the adhesive 314 does not extend to the second part 100b of the sensor. In this way, the thickness of the compressible layer 310 in the first part 100a is less than in the second part 100b. Moreover, the in-plane stiffness of the second part 100b (or modified second part 100b') is less than the in-plane stiffness of the first part 100a (or modified first part 100a') due to the absence of the adhesive 314 from the second part 100b.

However, preferably, the reinforcement structure 320 is a reinforcing in the sense that it is reasonably thick and reasonably hard. In terms of Young's modulus, the reinforcement structure 320 may be made of, or at least comprise, material that has a higher Youngs modulus than each one of: the compressible layer 310, the flexible and stretchable substrate 210 (if present), and the flexible and stretchable protective layer 230 (if present). The Young's modulus of the reinforcing structure 320 may be e.g. more than 15 MPa. A thickness of the reinforcement structure 320 is, in an embodiment, at least 0.1 mm; preferably at least 0.5 mm. The reinforcement structure 320 may comprise fibrous material, such as at least one of glass fibres, aramid fibres, and carbon fibres. The reinforcement structure 320 may comprise polymer, e.g. polymer having a Young's modulus of more than 15 MPa. Referring to FIG. 3f, the reinforcement structure 320 may be e.g. a package 422 for the other electronics, such as at least a part of a flexible board 410 and/or a rigid component 420. When a package 422 of the active electronics of the sensor 100 forms at least a part of the reinforcement structure 320, the reinforcement structure 320 may comprise polymer; e.g. polymer having a Young's modulus of more than 15 MPa; optionally reinforced with fibres as indicated above. The level of compressibility of the compressible layer 310 may be defined e.g. in terms of Young's modulus. In an embodiment, the Young's modulus of the compressible layer 310 is from 0.05 MPa to 15 MPa, such as from 0.2 MPa to 5 MPa. The electrical resistivity of the compressible layer 310 may be at least 10 Ωm at a temperature of 23° C. Moreover, as the layer 310 is compressible, it can be compressed by at least 10% in a reversible manner.

Same materials are suitable for the compressible layer 310 as for the substrate 210. Thus, in an embodiment, the material of the compressible layer 310 is selected from a group consisting of polyurethane, polyethylene, poly(ethylene-vinyl acetate), polyvinyl chloride, polyborodimethylsiloxane, polystyrene, acrylonitrile-butadiene-styrene, styrene-butadienestyrene, ethylene propylene rubber, neoprene, cork, latex, natural rubber, silicone, and thermoplastic elastomeric gel. Preferably, a thickness $T_{310a}$ of the compressible layer 310 is at least 0.5 mm.

As for suitable materials for the flexible circuit board 410, these include polyimide, polyethylene naphthalate, polyethylene terephthalate, and polyetheretherketone. In an embodiment, the flexible circuit board 410 comprises material selected from a group consisting of these materials. The flexibility of the flexible circuit board 410 is also a result of the board 410 being relatively thin. In an embodiment, the a thickness of the flexible circuit board 410 is less than 1 mm, such as at most 0.5 mm or less than 0.4 mm. In addition, the flexible circuit board 410 comprises electrically conductive wiring as indicated above.

Such materials are flexible, but not reversibly stretchable to a great extent. Some of the materials may be reversibly stretched for a few percents, but not as much as defined above for a stretchable material. Because of the low stretchability, traditional circuit board manufacturing techniques, such as etching, may be used to produce the flexible board 410 with wiring. Because of these manufacturing techniques and the wiring material, which is also not stretchable, the line width can be much smaller than that of the flexible and stretchable multilayer conductor structure 200. Therefore, in an embodiment, the flexible board 410 comprises electrically conductive wiring. An electric conductivity of the wiring of the flexible board 410 may be at least 1 S/m at a temperature of 23° C. In an embodiment, the first electrically conductive wire 222 has a first line width, and the wiring of the flexible board 410 comprises a wire with a second line width, wherein the second line width is less than the first line width.

Figure 5A:
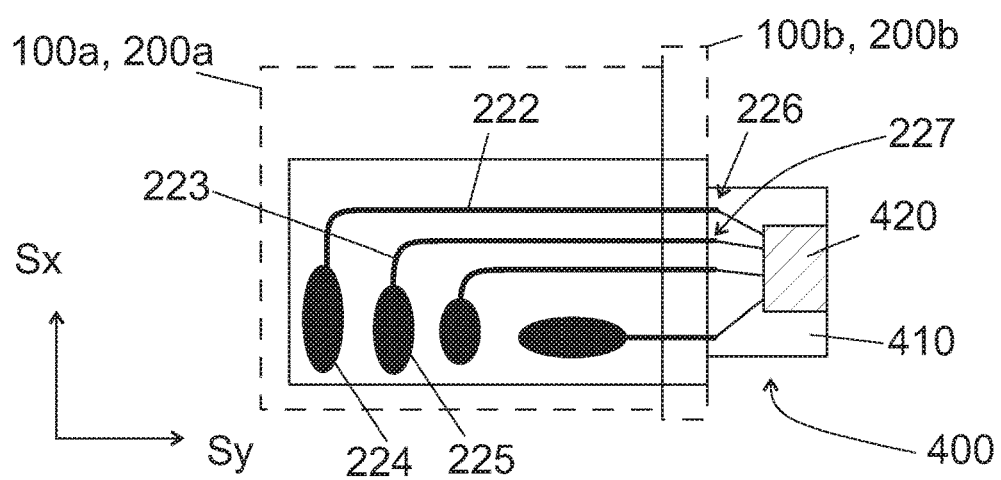
FIG. 5a shows in a top view a capacitive sensor 100.
Figure 5B:
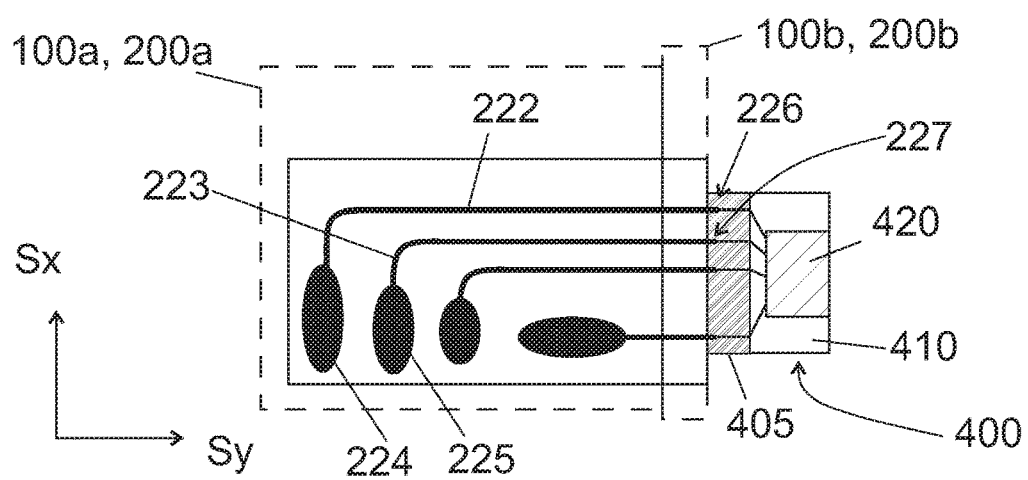
FIG. 5b shows in a top view a capacitive sensor 100.

Referring to FIGS. 5a and 5b, in an embodiment, the sensor 100 comprises a rigid component 420. The rigid component 420 is arranged outside of the first part 100a of the sensor 100. The rigid component 420 is electrically connected to the first joint 226. Typically the sensor 100 comprises also a second joint 227 and the rigid component 420 is electrically connected to also to the second joint 227, and via the second joint 227 to a second wire 223 and further to a second electrode 225. A rigid component refers to passive electronic component (e.g. connector) or an active electronic component (e.g. a chip). The term rigid component refers to a component, of which thickness (i.e. smallest of three perpendicular measures) is more than 0.1 mm and which comprises material having a Young's modulus of at least 1 GPa. In addition to the material with such a high Young's modulus, the rigid component may comprise another material with a lower Young's modulus. For example, the rigid component may comprise a chip comprising silicon in addition to some soft mechanical parts. It is noted that the elastic properties of crystalline silicon depend on the orientation, but in general they are in the range of from 60 GPa to 170 GPa. In an embodiment, a part of the reinforcement structure 320 overlaps with the rigid component 420. This improves the reliability also near the rigid component 420. In addition, in some application this improves the comfort of use, since the reinforcement structure 320 spreads the stress caused by the rigid component 420, e.g. if the sensor 100 is used in an insole or a mitt.

The rigid component 420 may comprise an electronic chip arrangement comprising of one or more electronic chips, and optionally packaging related thereto. The electronic chip arrangement is configured to measure the capacitance of the first electrode 224. As detailed above, preferably, the rigid component 420 is configured to measure the capacitance from the whole area of the first electrode 224 at one instance of time. More preferably, the rigid component 420 is configured to measure the capacitance from the whole area of the first electrode 224 at one instance of time and the capacitance from the whole area of the second electrode 225 at the same or another instance of time. The capacitance may be measured relative to surroundings or another electrode, such as a common potential electrode 340. The capacitance may be transferable to a receiver in an analog form. However, preferably the electronic chip arrangement is configured to convert the measured capacitance(s) to a digital signal. Preferably, the rigid component 420 comprises an electronic chip that is configured to convert capacitance(s) to digital form. Such chips are commonly known as a capacitance to digital converters (CDC). In an embodiment, the rigid component 420 comprises a capacitance to digital converter.

Referring to FIGS. 5a and 5b, in an embodiment, the sensor 100 comprises a flexible board 410 connected to the first electrically conductive wire 222 via the first joint 226. Moreover, in such an embodiment, the flexible board 410 is connected to the rigid component 420. Thus, the rigid component 420 is connected to the first joint 226 via the flexible board 410. Thus, the rigid component 420 may be connected to the second joint 227 via the flexible board 410. A wire-to-board connector can be used to connect the rigid component 420 to the flexible board 410. In an embodiment, at least a part of the flexible board 410 overlaps with a part of the reinforcement structure 320. This further improves the reliability near the first joint 226, i.e. between the multilayer structure 200 and the flexible board 410.

In an embodiment, the flexible board 410 is connected to the first electrically conductive wire 222 using suitable joining technique, such as crimp connection or conductive adhesive, such as anisotropic conductive adhesive (ACF). In such a case, the conductive adhesive may form the first joint 226 or a part thereof. Conductive adhesives have been found to form reliable joints. Most preferably, a part of the reinforcement structure 320 overlaps with the rigid component 420 and another part of the reinforcement structure 320 overlaps with at least a part of the flexible board 410. This improves the reliability both near the rigid component 420 and near the first joint 226. The flexible board 410 may be connected to the second wire 223 in a similar manner so as to form a part of the second joint 227.

Referring to FIGS. 6*a* and 6*b*, it has been noticed that the reliability near the first joint 226 can be further improved by making the first wire 222 to meander near the first joint 226. A meandering wire takes in mechanical stress even more effectively than a straight wire, even if stretchable. Therefore, in an embodiment and within the second part 100*b* of the capacitive sensor 100, the first electrically conductive wire 222 meanders. The first electrically conductive wire 222 may meander at least within the second part 100*b* such that the first electrically conductive wire extends from a first point P1 to a second point P2 in such a manner that a distance between these points (P1, P2), as measured along the first electrically conductive wire 222, is greater than the distance between these points (P1, P2) measured straight. Preferably, the first electrically conductive wire 222 meanders within the second part 100*b* such that the first electrically conductive wire extends from a first point P1 to a second point P2 in such a manner that a distance between these points (P1, P2), as measured along the first electrically conductive wire 222, is at least 5% greater than the distance between these points (P1, P2) measured straight. The second point P2 may be located at the first joint 226. The first point P1 may be located at the common edge 100*ab* of the first part 100*a* and the second part 100*b* of the sensor 100.

Referring to FIG. 6*a*, in an embodiment, the first electrically conductive wire 222 meanders (as seen from top) on the substrate 210, e.g. in between the substrate 210 and the protective layer 230. The substrate 210 needs not to meander, but it may meander. Thus, the wire 222 may meander (at least) in a tangential plane of the substrate 210. In addition or alternatively, the multilayer conductor structure 200 may meander in the direction Sz of thickness, as indicated in FIG. 6*b*. It has been noticed that the meandering particularly in the direction Sz of thickness of the sensor improves reliability, since a wire that meanders in the Sz direction is extremely resilient in the in-plane direction (i.e. perpendicular to Sz). The first electrically conductive wire 222 may meander, even if only one of or neither one of the substrate 210 and the protective layer 230 are used.

As motivated above, at least a part, e.g. more than a half, of the sensor 100 is conformable. However, the reinforcement structure 320 needs not to be conformable, or at least not as conformable as the rest of the sensor 100. Referring to FIG. 7, in an embodiment, the first electrically conductive wire 222 extends beyond an edge 322 of the reinforcement structure 320. Thus, a part of the first electrically conductive wire 222 does not overlap with the reinforcement structure 320. Moreover, in an embodiment, the reinforcement structure 320 does not overlap with a part of the first electrode 224. However, in an embodiment, the reinforcement structure 320 overlaps with the whole first electrode 224. Moreover, in an embodiment, the reinforcement structure 320 overlaps with all the electrodes (including 224 and 225). This may improve reliability.

In terms of cross sectional areas, in an embodiment, a cross-sectional area $A_{320}$ (see FIG. 12) of the reinforcement layer is at most 50% or at most 35% of a cross-sectional area $A_{200}$ (see FIG. 12) of the sensor 100 (e.g. the multilayer conductor structure 200). Herein the cross-sectional area refers to an area of a cross-section that is measured on a tangential surface of the sensor 100. In case the sensor 100 is substantially planar or can be brought to a substantially planar form, the cross-sectional area refers to an area of a cross-section on a plane having a normal in the direction Sz of the thickness of the sensor. Having this type of relatively small reinforcement layer improves the comfort of use of the sensor.

As indicated in many of the figures, a part of the reinforcement structure 320 may overlap with the first electrically conductive wire 222; however as indicated above, it needs not to overlap. In particular, the first electrically conductive wire 222 extends from the first joint 226 via the second part 200*b* of the multilayer conductor structure to the first part 200*a* of the multilayer conductor structure and further to the first electrode 224. In an embodiment, the first part 200*a* of the multilayer conductor structure 200 comprises a first part 222*a* of the first wire 222. In an embodiment, the second part 200*b* of the multilayer conductor structure 200 comprises a second part 222*b* of the first wire 222. In addition to the first wire 222, also the substrate 210 and the protective layer 230 may extend beyond the edge 322 of the reinforcement structure 320. Moreover, in this embodiment, also the compressible layer 310 extends beyond the edge 322 of the reinforcement structure 320. As indicated in FIGS. 8*a*1 to 8*b*2, in such a case, the sensor 100 is further dividable to a third part 100*c*, which extends through the sensor 100 in a direction Sz of thickness of the sensor 100, and which does not comprise a part of the reinforcement structure 320. Moreover, the third part 100*c* of the sensor has a third in-plane elastic modulus $Y_{100c}$. The third in-plane elastic modulus $Y_{100c}$ may be the same or substantially same as the first in-plane elastic modulus $Y_{100c}$ of the modified first part 100*a'*, i.e. the first part 100*a* without the reinforcing structure 320. In the alternative, as indicated above and in particular in connection with touch sensors, the compressible layer 310 and the common potential electrode 340 need not extend beyond the edge 322. In such a case, the in-plane stiffness of the third part 100*c* would be less than the in-plane stiffness of the modified first part 100*a'*.

As indicated above, the accuracy of the measurements may be improved by measuring a capacitance between two electrodes. The other one of the two electrodes may be referred to as a first common potential electrode 340 (see FIGS. 8*a*1 and 8*b*1). In case the potential of the first common potential electrode 340 is set to a ground potential, the electrode may be referred to as a first ground electrode. The first common potential electrode 340 may serve as an electrode that is common to a first pair of electrodes (including the first common potential electrode 340 and the first electrode 224) and a second pair of electrodes (including the first common potential electrode 340 and the second electrode 225). When a part of the compressible layer 310 is left in between the first common potential electrode 340 and the first electrode 224, in particular the capacitance of the first electrode 224 relative to the first common potential electrode 340 can be measured.

Thus, in an embodiment, the sensor 100 comprises a first common potential electrode 340. Moreover, a part of the compressible layer 310 is arranged in between the first common potential electrode 340 and the first electrode 224. In this way, a measurable capacitance is formed in between the first common potential electrode 340 and the first electrode 224. Preferably, these layers of the sensor 100 are arranged relative to each other such that at least a part of the first common potential electrode 340 overlaps with at least a part of the first electrode 224. Moreover, a part of the compressible layer 310 is arranged in between the first common potential electrode 340 and the first electrode 224 in the direction Sz of the thickness of the sensor 100. More preferably, at least a part of the first common potential electrode 340 overlaps with the whole first electrode 224. In an embodiment, first common potential electrode 340 is connected to the rigid component 420. The first common potential electrode 340 may overlap also the second electrode 225 in a similar manner mutatis mutandis.

The first common potential electrode 340 may be uniformly conductive, e.g. made using conductive ink, paste, or conductive polymer on a uniform surface. As for the conductive material, the materials that are suitable for the first wire 222 (as discussed above), are suitable also for the conductive material of the first common potential electrode 340. In the alternative, the first common potential electrode 340 may be a mesh of conductive yarns, e.g. made using conductive ink or paste or filaments. It may also suffice that the first common potential electrode 340 consists of a meandering electrically conductive line. It may also suffice that the first common potential electrode 340 comprises multiple separate electrically conductive lines. In an embodiment, at least a part of the first common potential electrode 340 is made from a conductive ink. In an embodiment the first common potential electrode 340 comprises electrically conductive fabric. In an embodiment, the first common potential electrode 340 comprises electrically conductive polymer (e.g. polyaniline, polyvinyl, PEDOT:PSS or a polymer with conductive particles).

Referring to FIGS. 4a to 4d, the reliability of the sensor 100 may be further improved by applying a spacer layer 330. The spacer layer 330 may serve as the neighboring layer discussed above. When the spacer layer 330 is attached to the first wire 222, optionally via other parts of a multilayer structure 200, also the spacer layer 330 provides for mechanical support for the wire 222, and in this way improves reliability, at least when resilience in the second part 100b is not compromised. As indicated in the figure, at least a part of the first wire 222 is arranged in between the compressible layer 310 and the spacer layer 330 in the direction Sz of the thickness Sz of the sensor.

The material of the spacer layer 330 may be selected according to needs. In case the spacer layer 330 needs to be conformable and/or configured to be compressed in use, the material of the spacer layer 330 may be selected from the group consisting of polyurethane, polyethylene, poly(ethylene-vinyl acetate), polyvinyl chloride, polyborodimethylsiloxane, polystyrene, acrylonitrile-butadiene-styrene, styrene-butadienestyrene, ethylene propylene rubber, neoprene, cork, latex, natural rubber, silicone, and thermoplastic elastomeric gel. However, in case it suffices that the spacer layer 330 is flexible, also a material selected from the group consisting of polyimide, polyethylene naphthalate, polyethylene terephthalate, and polyetheretherketone can be used; in addition to some other flexible materials. Furthermore, in cases, where the spacer layer 330 needs not be even flexible, also epoxy and/or phenolic resin may be used as the material of the spacer layer 330. Preferably the spacer layer 330 is at least flexible, and more preferably also stretchable. In case the spacer layer 330 is not even flexible, the whole sensor 100 may be rigid, in which case the structure itself does not so easily show mechanical reliability problems. In this way, in a preferable embodiment, at least a part of the sensor 100, such as least a half of the cross-section of the sensor 100, is flexible in the meaning defined above. Moreover, in another preferable embodiment, at least a part of the sensor 100, such as least a half of the cross-section of the sensor 100 is flexible and stretchable in the meanings defined above. A thickness of the spacer layer 330 may be e.g. at least 0.1 mm, such as at least 0.5 mm. If the spacer layer 330 is used as a layer that deforms in use, whereby e.g. a capacitance if the first electrode relative to e.g. a second common potential electrode 350 also changes in use, a thickness of the spacer layer 330 is preferably at least 0.5 mm. As for materials suitable for such use, the materials suitable for the compressible layer 310 are usable also for the spacer layer 330, as indicated above.

Figure 9B:
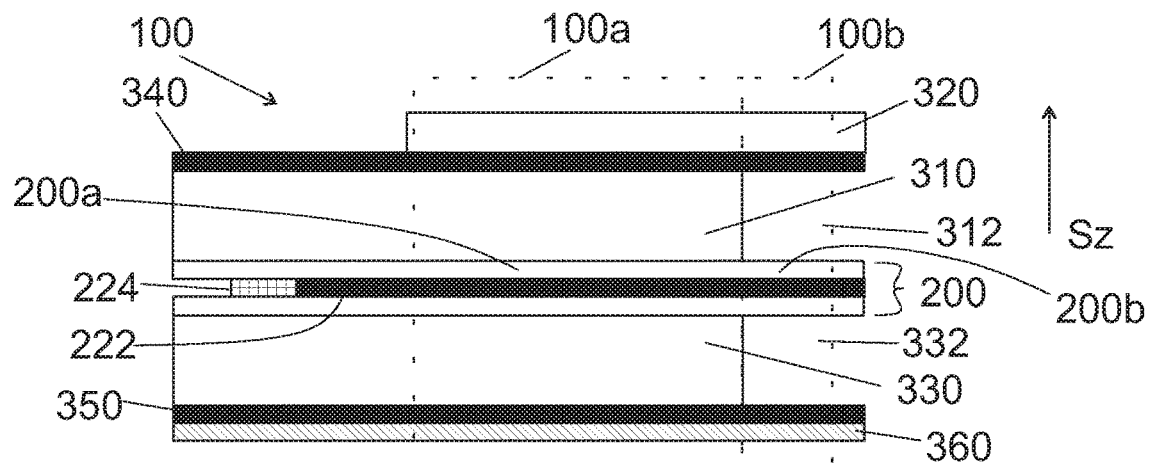
Figure 9C:
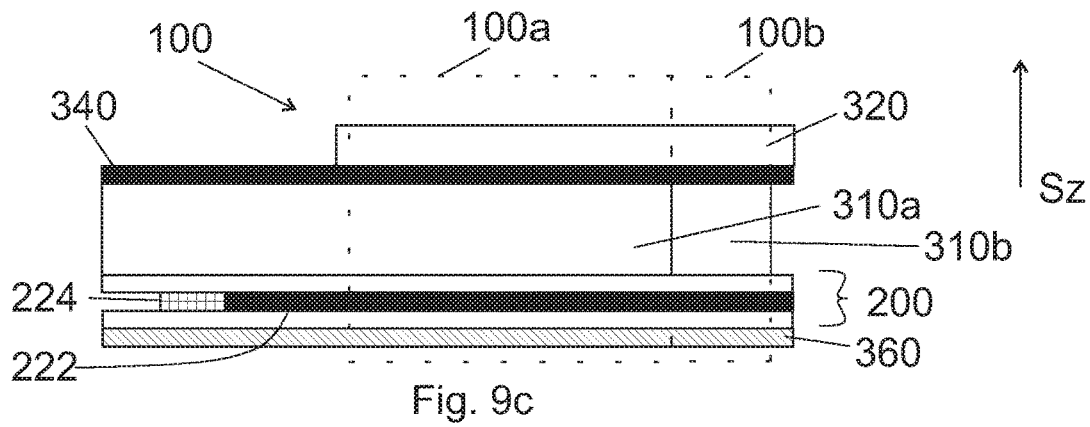

In case the spacer layer 330 extends to the second part 100b of the sensor, as in FIGS. 4a, 4b, and 9c, the material of the second part 330b of the spacer layer 330, which second part 330b is comprised by the second part 100b of the sensor 100, the second part 330b is preferably made of softer material than the first part 330a of the spacer layer 330, which first part 330a is comprised by the first part 100a of the sensor 100. In the alternative, relative resilience can be improved by having the spacer layer 330 in the first part 100a of the sensor such that the spacer layer 330 does not extend to the second part 100b of the sensor (see FIG. 8b1).

Referring to FIGS. 8b1, 9b, 9d, 10, and 11, in an embodiment, the capacitive sensor comprises a second common potential electrode 350. Moreover, a part of the spacer layer 330 is arranged in between the second common potential electrode 350 and the first electrode 224. In this way, another capacitance of the first electrode 224, i.e. its capacitance relative to the second common potential electrode 350, can be measured. Moreover, the other capacitance is sensitive to pressure, when at least a part of the second common potential electrode 350 overlaps with at least a part of the first electrode 224. Thus, in an embodiment at least the parts of these electrodes 224, 350 overlap in such a way. The second common potential electrode 350 may overlap the second electrode 225 in a similar manner mutatis mutandis. What has been said about the material of the first common potential electrode 340 applies to the material of the second common potential electrode 350.

Referring to FIGS. 2a, 5a, 5b, and 6a, preferably the multilayer conductor structure 200 comprises a second electrically conductive wire 223. At least a part of the second electrically conductive wire 223 may be arranged on the flexible and stretchable substrate 210, such as in between the flexible and stretchable substrate 210 and the flexible and stretchable protective layer 230. The second electrically conductive wire 223 is attached to a second joint 227 for connecting the second wire 223 to the other electrically conductive structure 400, such as a flexible circuit board 410 or a connector 405. Moreover, the second electrically conductive wire 223 extends from the second joint 227 via the second part 100b of the sensor to the first part 100a of the sensor and further to the second electrode 225. In an embodiment, the first part 100a of the sensor comprises a first part of the second wire 223. In an embodiment, the second part 100b of the sensor comprises a second part of the second wire 223. Also the second wire 223 is flexible and stretchable in the meaning discussed above for these terms. What has been said about the material of the first wire 222 applies to the material of the second wire 223. Preferably the second electrode 225 is also flexible and stretchable in the meaning discussed above for these terms. What has been said about the material of the first electrode 224 applies to the material of the second electrode 225.

Referring to FIGS. 9a and 9b in an embodiment, the sensor 100 comprises a bottom layer 360. A part of the compressible layer 100 is arranged in between the reinforcement structure 320 and the bottom layer 360. In FIGS. 9a and 9b, a part of the first wire 222 is arranged in between the reinforcement structure 320 and the bottom layer 360. In order to reduce the second in-plane stiffness, a gap 312 is arranged between the second part 320b of the reinforcement structure 320 and the second part 222b of the first wire 222. Thus, the gap 312 is also arranged in between the second part 320b of the reinforcement structure 320 and the bottom layer 360. In FIG. 9b, also a gap 332 is arranged between second part 320b of the reinforcement structure 320 and the bottom layer 360. Such a gap (312, 332) is left, in the direction Sz of thickness, at the same level as the neighboring layer (310, 330). Correspondingly, a gap 312 may be left at the level of the compressible layer 310. The level herein indicate a distance from the reinforcement structure 320 in the direction Sz of thickness of the sensor. In a similar manner, a gap 332 may be left at the level of the spacer layer 330.

Figure 9D:
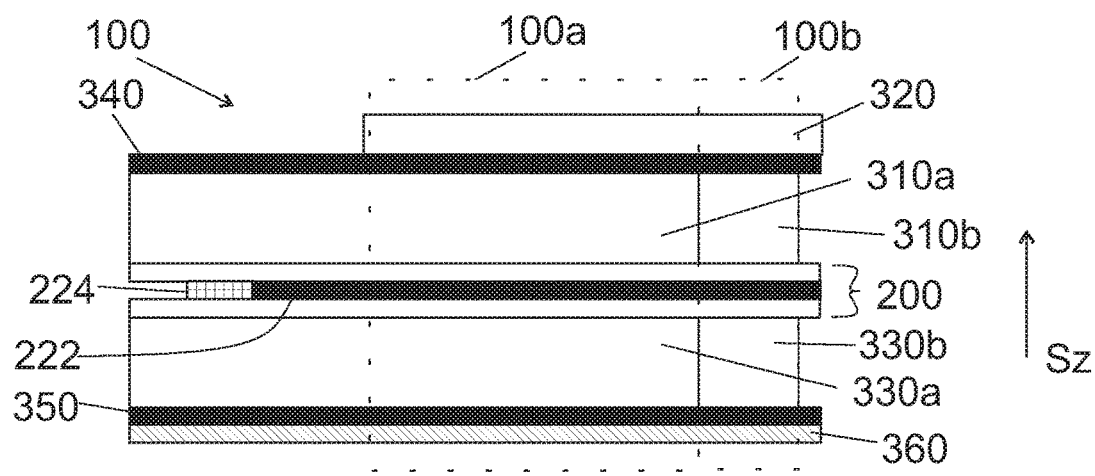

However, referring to FIGS. 9c and 9d at least one of the gaps 312, 332 may be filled with soft material to form a second part or second parts 310b, 330b of the compressible layer 310 and/or the spacer layer 330. If the material of the second part 310b of the compressible layer 310 is softer than the material of the first part 310a of the compressible layer 310, the in-plane elastic modulus $Y_{100b}$ of the modified second part 100b' of the sensor is smaller than the in-plane elastic modulus $Y_{100a}$ of the modified first part 100a' of the sensor. In this way, the second part 200b of the multilayer conductor structure is configured to take in mechanical deformation in use. Herein the first part 100a of the sensor 100 comprises the first part 310a of the compressible layer 310 and the second part 100b of the sensor 100 comprises the second part 310b of the compressible layer 310. In this case the material of the neighboring layer 310 is softer within the second part 100b of the capacitive sensor 100 than the material of the neighboring layer 310 within the first part 100a of the capacitive sensor 100.

The same finding applies also to the spacer layer 330. If the material of the second part 330b of the spacer layer 330 is significantly softer than the material of the first part 330a of the spacer layer 330, the second part 200b of the multilayer conductor structure is configured to take in the mechanical deformations. Herein the first part 100a of the sensor 100 comprises the first part 330a of the spacer layer 330 and the second part 100b of the sensor 100 comprises the second part 330b of the spacer layer 330. In this case the material of the neighboring layer 330 is softer within the second part 100b of the capacitive sensor 100 than the material of the neighboring layer 330 within the first part 100a of the capacitive sensor 100. The material of the second part 330b of the spacer layer 330 (if present) may have a lower Young's modulus than the material of the first part 330a of the spacer layer 330, e.g. at least 25% lower.

Figure 10:
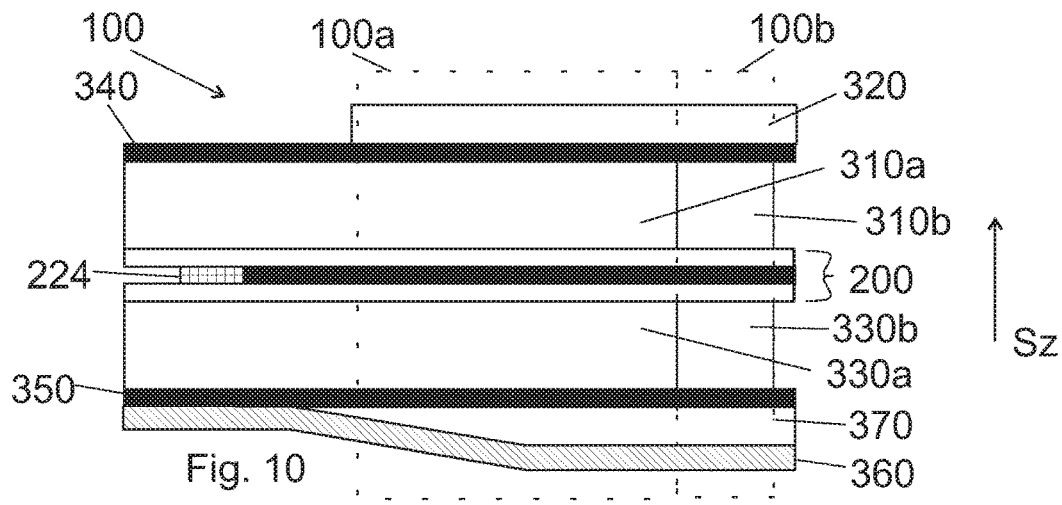
FIG. 10 shows in side view parts of a capacitive sensors 100.

The sensor 100 may comprise further layers. Referring to FIG. 10, the sensor 100 may comprise a second reinforcement structure 370, such as a second reinforcement layer 370; in which case the reinforcement structure 320 may be referred to as a first reinforcement structure 320. A part of the first wire 222 and a part of the compressible layer 310 are arranged in between the (first) reinforcement structure 320 and the second reinforcement structure 370. At least a part of the common potential electrode 340, if present, may be arranged in between the first reinforcement structure 320 and the second reinforcement structure 370. At least a part of the second common potential electrode 350, if present, may be arranged in between the first reinforcement structure 320 and the second reinforcement layer structure. At least a part of the spacer layer 330, if present, may be arranged in between the first reinforcement structure 320 and the second reinforcement structure 370. Herein the term "in between" refers to the direction Sz of thickness. However, if the sensor 100 comprises both the second reinforcement structure 370 and the bottom layer 360, preferably, both the first reinforcement structure 320 and the second reinforcement structure 370 are arranged on a same side of the bottom layer 360. Thus, the bottom layer 360 may be finished e.g. for visual appearance of the sensor and/or for improved comfort of use. The second reinforcement structure 370 may be made of such a material that has been discussed above to be suitable for the first reinforcement structure 320.

Referring to FIG. 11, the sensor 100 may comprise a top layer 380. The reinforcement structure 320, a part of the first wire 222, and a part of the compressible layer 310 are arranged on a same side of the top layer 380. Thus, the top layer 380 may be finished e.g. for visual appearance of the sensor and/or for improved comfort of use. Preferably, the top layer 380 is made of textile (synthetic or natural). In an embodiment, the top layer 380 comprises fibrous material. In an embodiment, the top layer 380 comprises woven fibrous material. The sensor may comprise the top layer 380 even if does not comprise one or more than one of the following layers: the second reinforcement layer 370, the bottom layer 360, the (first) common potential electrode 340, the second common potential electrode 350, and the spacer layer 330.

Thus, as discussed in detail above, the reliability may be improved by allowing the second part 222b of the first electrically conductive wire 222 to move relatively freely in relation to the reinforcement structure. The following two alternatives were identified:

using a layer (310, 330), of which at least a part does not extend in a lateral direction (i.e. perpendicular to the direction Sz of thickness) as far as the wire 222. As a result a gap 312, 332 is formed, which in effect reduces the in-plane stiffness of the second part 100b; and using a softer material for the layer (310, 330) within the second part 100b than within the first part 100a.

As for the first option, it suffices that a thin part (e.g. the body 310') of the layer (310, 330) extends in the lateral direction when another part (e.g. adhesive 314) does not extend, thereby forming a gap.

Even if not shown in the figures, it is possible to use a layer (310, 330) having both a soft area (310b, 330b, e.g. within the second part 100b) and a hard area (within the first part 100a), and to further have such a gap (312, 332) that the gap is left between the joint 226 and the soft are (310b, 330b).

Moreover, as discussed in detail above, the reliability may be further improved, on one hand, by attaching in the direction Sz of the thickness, within the first part 100a, the first electrically conductive wire 222 to the reinforcement structure 320 and by not attaching the first electrically conductive wire 222 to the reinforcement structure 320 within the second part 100b in the direction Sz of the thickness. Not attaching may be achieved by using a gap (312, 332) or, in case the gap is filled, not attaching the material that fills the gap to at least a layer next to the material that fills the gap.

Furthermore, the in-plane stiffness of the modified parts (100a', 100b') may be engineered as discussed above to further improve reliability. Possibilities include engineering the elastic moduli ($Y_{100a}$, $Y_{100b}$) of the modified parts (100a', 100b') and/or engineering the thicknesses of the modified parts (100a', 100b').

Such a sensor can be used in various application including, but not limited to, clothing, such as gloves, mitts, footwear (shoes, insoles, socks), helmets, etc. In clothing, particularly two applications may be pointed out: a boxing glove and an insole for footwear. Other applications include scales for measuring mass and tactile sensors e.g. for various user interface devices.

Figure 12:
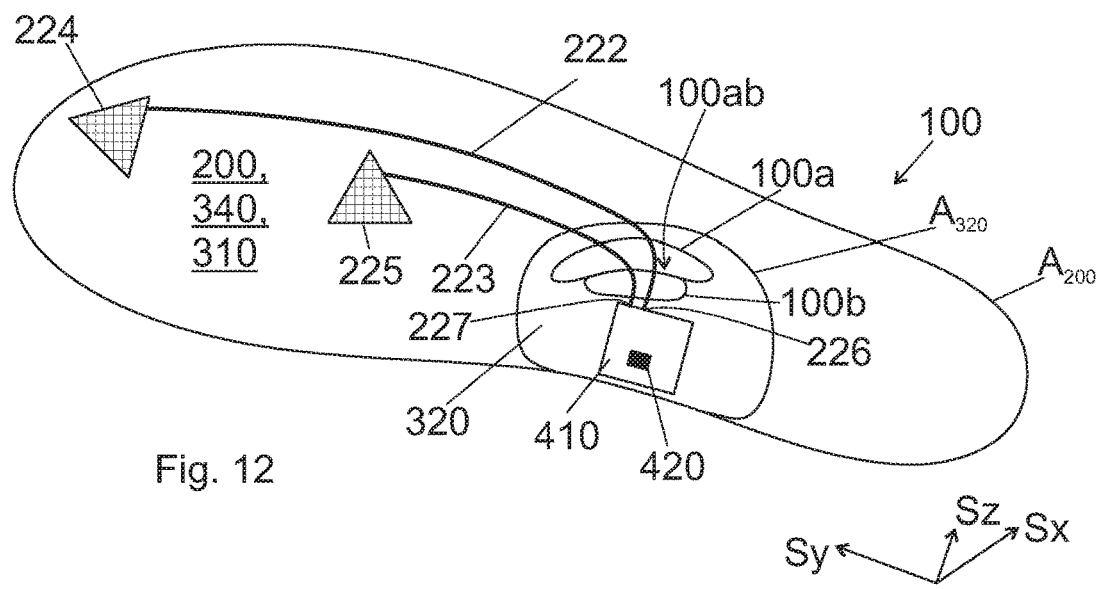
FIG. 12 shows a capacitive sensor for use as an insole.

To this end, FIG. 12 shows a sensor 100, the sensor 100 being shaped as an insole for footwear. The measuring electronics, including a rigid component 420, such as a chip, is arranged at a location, which in use, is arranged beneath the arch of a foot. The component 420 is attached to a flexible board 410, which is attached to a first wire 222 of a multilayer conductor structure, which is flexible and stretchable. The component 420, the flexible board 410, and a part of the first wire 222 are arranged beneath a reinforcement structure 320. The sensor 100 extends laterally outside the reinforcing layer 320, and comprises—also outside the reinforcement structure 320—a part of the multilayer conductor structure 200 and a part of the compressible layer 310; and typically also a part of the common potential electrode 340. The first electrode 224 forms a part of the wiring of the multilayer conductor structure 200, and is arranged in between the flexible and stretchable substrate 210 and the flexible and stretchable protective layer 230. A possible selection of the first part 100a and the second part 100b of the sensor 100 are indicated in FIG. 12. As indicated above, both the first and second parts (100a, 100b) are selected such that both of them comprise a part of the reinforcement structure 320. As discussed above, an in-plane elastic modulus $Y_{100a}$ of the modified first part 100a' may be greater than an in-plane elastic modulus $Y_{100b}$ of the modified second part 100b'. Moreover, in the embodiment of FIG. 12, within the first part 100a, the multilayer conductor structure 200 is attached to the compressible layer 310, e.g. using an adhesive. In addition, outside the reinforcement structure 320, the multilayer conductor structure 200 is attached to the compressible layer 310. When the sensor is used as an insole, the multilayer conductor structure 200 takes in stress by deformations due to the different in-plane elastic moduli. Even if FIG. 12 shows a sensor 100 with only two electrodes, the sensor can be provided with multiple electrodes according to needs. For example, the sensor 100 may be provided with an electrode configuration disclosed in the patent FI 127245.

Figure 13A:
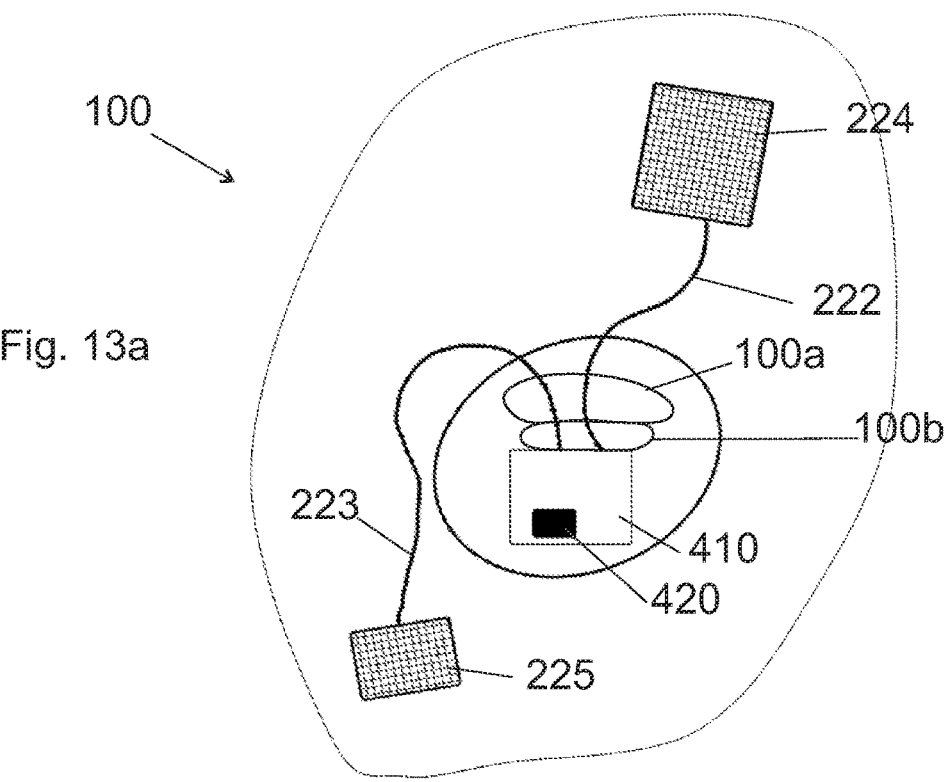
FIGS. 13a and 13b show capacitive sensors for other uses.
Figure 13B:
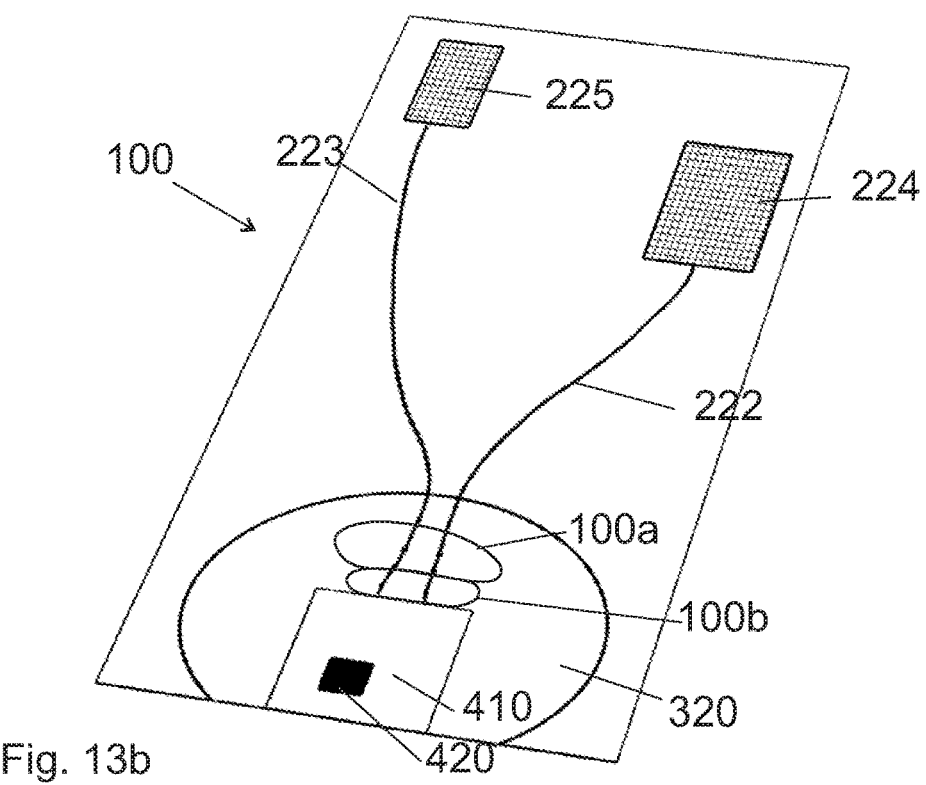

FIGS. 13a and 13b show some other shapes for the sensor for other applications than an insole.

The invention claimed is:
1. A capacitive sensor, comprising:
a first electrically conductive wire that is flexible and stretchable,
a compressible layer,
an integral reinforcement structure, and
a first electrode for measuring a capacitance and coupled to the first electrically conductive wire, wherein the capacitive sensor further comprises
a first part of the capacitive sensor, the first part extending through the sensor in a direction (Sz) of thickness of the sensor, the first part of the capacitive sensor comprising
a first part of the reinforcement structure,
a first part of the first electrically conductive wire, and
a first part of the compressible layer, such that
at least a part of the first part of the reinforcement structure overlaps with at least a part of the first part of the compressible layer in the direction (Sz) of thickness of the sensor and
at least a part of the first part of the compressible layer overlaps with at least a part of the first part the first electrically conductive wire in the direction (Sz) of thickness of the sensor, and
a second part of the capacitive sensor, the second part extending through the sensor in a direction (Sz) of thickness of the sensor, the second part of the capacitive sensor comprising
a second part of the reinforcement structure, and
a second part of the first electrically conductive wire, wherein
the first electrically conductive wire is attached to a first joint for connecting the first wire,
the first electrically conductive wire extends from the first joint via the second part of sensor to the first part of the sensor and further to the first electrode, and
the second part of the sensor comprises a second part of the compressible layer, wherein an in-plane stiffness of the second part of the compressible layer is less than an in-plane stiffness of the first part of the compressible layer, or
the compressible layer does not extend to the second part of the sensor.

2. The capacitive sensor of claim 1, wherein
a Young's modulus of the second part of the compressible layer is less than a Young's modulus of the first part of the compressible layer and/or
a thickness of the second part of the compressible layer is less than a thickness of the first part of the compressible layer.

3. The capacitive sensor of claim 1, wherein
within the first part of the sensor, the first part of the first electrically conductive wire is attached, directly or via at least one layer, to the first part of the reinforcement structure in a direction (Sz) of thickness of the sensor and
within the second part of the sensor, the second part of the first electrically conductive wire is not attached, directly or via at least one layer, to the second part of the reinforcement structure in the direction (Sz) of thickness of the sensor.

4. The capacitive sensor of claim 1, comprising:
a flexible board connected to the first electrically conductive wire.

5. The capacitive sensor of claim 1, comprising:
a rigid component that is
arranged outside the first part of the capacitive sensor and
electrically connected to the first joint.

6. The capacitive sensor of claim 4, comprising:
a rigid component that is
arranged outside the first part of the capacitive sensor and
electrically connected to the first joint; wherein the flexible board is connected to the first electrically conductive wire, and the flexible board is connected to the rigid component.

7. The capacitive sensor of claim 1, comprising:

a multilayer conductor structure, comprising a flexible and stretchable substrate, wherein the first electrically conductive wire is arranged on the substrate.

8. The capacitive sensor of claim 1, wherein within the second part of the capacitive sensor, the first electrically conductive wire meanders.

9. The capacitive sensor of claim 8, wherein within the second part of the capacitive sensor, the first electrically conductive wire meanders in the direction (Sz) of thickness of the sensor.

10. The capacitive sensor of claim 1, wherein at least a part of the second part of the sensor is arranged in a direction perpendicular to the direction (Sz) of thickness of the sensor in between the first joint and the first part of the sensor and a length of such a part of the first wire that extends within the second part is greater than a thickness of the compressible layer within the first part.

11. The capacitive sensor of claim 1, comprising:

a first common potential electrode, such that a part of the compressible layer is arranged in between the first common potential electrode and the first electrode in the direction (Sz) of thickness of the sensor.

12. The capacitive sensor of claim 1, comprising:

a spacer layer such that at least a part of the first electrically conductive wire is arranged in the direction (Sz) of thickness of the sensor in between the compressible layer and the spacer layer.

13. The capacitive sensor of claim 12, comprising:

a second common potential electrode such that a part of the spacer layer is arranged in the direction (Sz) of thickness of the sensor in between the second common potential electrode and the first electrode.

14. The capacitive sensor of claim 1, comprising:

a second electrode and a second electrically conductive wire, wherein the second electrically conductive wire is attached to a second joint for connecting the second electrically conductive wire, the second electrically conductive wire extends from the second joint via the second part of the multilayer conductor structure to the first part of the multilayer conductor structure and further to the second electrode.

* * * * *